(12) United States Patent
Choi et al.

(10) Patent No.: US 12,270,614 B2
(45) Date of Patent: Apr. 8, 2025

(54) SYSTEM AND MODULE FOR AUTOMATICALLY WASHING AND STERILIZING HEAT EXCHANGER OF SYSTEM AIR CONDITIONER

(71) Applicants: Sang Pil Choi, Incheon (KR); Sang Mu Choi, Busan (KR)

(72) Inventors: Sang Pil Choi, Incheon (KR); Sang Mu Choi, Busan (KR)

( * ) Notice: Subject to any disclaimer, the term of this patent is extended or adjusted under 35 U.S.C. 154(b) by 842 days.

(21) Appl. No.: 17/444,489

(22) Filed: Aug. 5, 2021

(65) Prior Publication Data

US 2022/0090870 A1 Mar. 24, 2022

(30) Foreign Application Priority Data

Sep. 22, 2020 (KR) .................... 10-2020-0122414
Mar. 24, 2021 (KR) .................... 10-2021-0037830

(51) Int. Cl.
*F28G 9/00* (2006.01)
*A61L 2/06* (2006.01)
(Continued)

(52) U.S. Cl.
CPC .................. *F28G 9/00* (2013.01); *A61L 2/06* (2013.01); *A61L 2/07* (2013.01); *B05B 1/005* (2013.01);
(Continued)

(58) Field of Classification Search
CPC .. B08B 3/02; B08B 3/024; B08B 5/02; B08B 13/00; B08B 15/02; B08B 17/00;
(Continued)

(56) References Cited

U.S. PATENT DOCUMENTS

2003/0024552 A1 2/2003 Watanabe

FOREIGN PATENT DOCUMENTS

CN 1740730 A 3/2006
CN 103153492 A 6/2013
(Continued)

OTHER PUBLICATIONS

Machine Translation of Imao et al, JP 08178590, Jul. 1996. (Year: 1996).*

(Continued)

*Primary Examiner* — David G Cormier
(74) *Attorney, Agent, or Firm* — Lippes Mathias LLP

(57) ABSTRACT

A system for automatically washing and sterilizing a heat exchanger of a system air conditioner is proposed. The system for automatically washing and sterilizing a heat exchanger of a system air conditioner according to an embodiment includes: a washer body including an air compressor, a compressed air tank, a detergent liquid tank, a washing water tank, a washing water tank, a high-pressure pump, a hot air generator, a steam generator, and a hot air generator; a washing module that sprays washing water, etc., supplied from the ground during rotation thereof to a cooling fin by a spray nozzle, thus washing the cooling fin; a waste water collection vinyl cover that collects waste water dropping when the cooling fin is washed; and a controller configured to control the washing module that sprays washing water, etc., to the cooling fin.

6 Claims, 27 Drawing Sheets

(51) Int. Cl.
  *A61L 2/07* (2006.01)
  *B05B 1/00* (2006.01)
  *B05B 13/04* (2006.01)
  *B08B 3/02* (2006.01)
  *B08B 5/02* (2006.01)
  *B08B 9/023* (2006.01)
  *B08B 13/00* (2006.01)

(52) U.S. Cl.
  CPC .......... *B05B 13/0421* (2013.01); *B08B 3/024* (2013.01); *B08B 5/02* (2013.01); *B08B 9/023* (2013.01); *B08B 13/00* (2013.01); *A61L 2202/14* (2013.01); *A61L 2202/15* (2013.01); *A61L 2202/17* (2013.01); *B08B 2203/007* (2013.01); *B08B 2209/032* (2013.01)

(58) Field of Classification Search
  CPC ...... B08B 2203/007; B08B 2203/0229; B08B 2215/00; F24F 2221/22; F24F 2221/225; A61L 2202/14; A61L 2202/15; A61L 2202/17; B05B 1/005; B05B 13/0421
  See application file for complete search history.

(56) References Cited

FOREIGN PATENT DOCUMENTS

| | | |
|---|---|---|
| JP | H06123437 A | 5/1994 |
| JP | H07103690 A | 4/1995 |
| JP | H08178590 A | 7/1996 |
| JP | H08296993 A | 11/1996 |
| JP | 2004333032 A | 11/2004 |
| JP | 2006064227 A | 3/2006 |
| JP | 2011002149 A | 1/2011 |
| JP | 2011058646 A | 3/2011 |
| KR | 10-0427799 B1 | 4/2004 |
| KR | 10-2008-0007255 A | 1/2008 |
| KR | 20120034333 A | 4/2012 |
| KR | 10-1237310 B1 | 2/2013 |
| KR | 101360787 B1 | 2/2014 |
| KR | 10-2016-0109789 A | 9/2016 |
| KR | 10-2017-0137486 A | 12/2017 |
| KR | 20170137486 A | 12/2017 |
| KR | 1020180004976 A | 1/2018 |
| KR | 10-2020-0008767 A | 1/2020 |
| KR | 10-2020-0046257 A | 5/2020 |
| KR | 20200001801 U | 8/2020 |
| WO | 2012044114 A2 | 4/2012 |

OTHER PUBLICATIONS

Office Action for Korean Application No. 10-2020-0122414, dated Jan. 12, 2021, 5 pages.
Office Action for Korean Application No. 10-2020-0122414, dated May 21, 2021, 6 pages.
Decision to Grant Chinese Patent Application No. 202110890859.4, dated Jun. 17, 2024, 3 pages.
Office Action for Chinese Patent Application No. 202110890859.4, dated Jan. 16, 2024, 54 pages.
Search Report for European Patent Application No. 21189958.8, dated May 11, 2022, 10 pages.
Combined Search and Examination Report for GB Patent Application No. 2113337.6, dated Jan. 27, 2022, 7 pages.
Examination Report for GB Patent No. 2113337.6, dated Nov. 22, 2022, 3 pages.
Office Action for Japanese Patent Application No. 2021-127483, dated Aug. 22, 2022, 12 pages.
Decision to Grant Japanese Patent Application No. 2021-127483, dated May 24, 2023, 5 pages.
Office Action for Korean Patent Application No. 1020200122414, dated Jan. 12, 2021, 10 pages.
Decision to Grant Korean Patent Application No. 1020200122414, dated Sep. 8, 2021, 3 pages.
Office Action for Korean Patent Application No. 1020210037830, dated Mar. 24, 2021, 6 pages.
Decision to Grant Korean Patent Application No. 1020210037830, dated May 17, 2023, 2 pages.
Office Action for Korean Patent Application No. 1020200122414, dated May 21, 2021, 11 pages.

* cited by examiner

SYSTEM AND MODULE FOR AUTOMATICALLY WASHING AND STERILIZING HEAT EXCHANGER OF SYSTEM AIR CONDITIONER

CROSS REFERENCE TO RELATED APPLICATION

This application is based on and claims priority from Korean Patent Applications Nos. 10-2020-0122414 filed on Sep. 22, 2020 and 10-2021-0037830 filed on Mar. 24, 2021 in the Korean Intellectual Property Office, the disclosure of which is incorporated herein in its entirety by reference.

BACKGROUND OF THE INVENTION

Field of the Invention

The present disclosure relates to a system air conditioner and, more particularly, to a system and module for automatically washing and sterilizing a heat exchanger of a system air conditioner, the system and module automatically washing out contaminants such as dust, grease, mold, and bacteria collected in the heat exchanger of an air conditioner, and automatically sterilizing and drying the heat exchanger.

Description of the Related Art

Unless stated otherwise in this specification, the contents described in this section are not the related art about the claims of this application and not all of the contents included in this section are regarded as the related art.

In general, air conditioners, depending on the installation types, are classified into a window type, a wall-mounted type, a stand type, and a ceiling type.

When a ceiling type air conditioner is operated with contaminants and odor-producing substances such as mold sticking to the heat exchanger (a cooling fin) thereof, it causes and aggravates asthma or atopic dermatitis and causes acute pneumonia of infants or children who have weak immune systems, so diseases related to the respiratory system may be increased.

Further, an awareness of cleanliness of ceiling type air conditioners is increasing, so it is important to keep the ceiling type air conditioners completely clean by washing them.

When ceiling type air conditioners are operated with contaminants such as dust and grease collecting and sticking to the heat exchanger thereof, the thermal efficiency of the heat exchanger decreases and the interior air is contaminated, so the heat exchanger should be washed.

Since electronic devices such as a personal computer (PC), a water purifier, etc. are placed under a ceiling type air conditioner in offices, tables equipped with a roaster are placed under a ceiling type air conditioner in restaurants, and food, etc. are placed under a ceiling type air conditioner in markets, when the heat exchanger of the ceiling type air conditioners is washed and washing water (waste water) drops down, a secondary damage may be generated.

Accordingly, since it is required to separate the heat exchanger of a ceiling type air conditioner, wash the heat exchanger, and then install the heat exchange back in the ceiling, this work is difficult and washing of ceiling type air conditioners installed at small places is almost ignored.

An apparatus equipped with a separable washing head for washing the heat exchanger of a 4-way system air conditioner has been disclosed in Korean Patent Application Publication No. 10-2020-0046257.

SUMMARY OF THE INVENTION

An embodiment of the present disclosure relates to a system and module for automatically washing and sterilizing a heat exchanger of a system air conditioner, the system and module automatically washing out contaminants such as dust, grease, mold, and bacteria collected in a heat exchanger of a ceiling type air conditioner, and automatically sterilizing drying the heat exchanger within short time with the heat exchanger installed so that personnel expenses can be reduced.

An embodiment of the present disclosure relates to a system and module for automatically washing and sterilizing a heat exchanger of a system air conditioner, the system and module being able to prevent a secondary damage due to contaminated washing water when washing an air conditioner installed in an office with a plurality of personal computers under a heat exchanger or washing a heat exchanger installed in the ceiling of a market with foods, etc.

An embodiment of the present disclosure relates to a system and module for automatically washing and sterilizing a heat exchanger of a system air conditioner, the system and module being able to store and provide in real time a process of washing, sterilizing, and drying a heat exchanger and an operation graph related to the temperature in the washing process and the operation time to customers.

An embodiment of the present disclosure relates to a system and module for automatically washing and sterilizing a heat exchanger of a system air conditioner, the system and module including a washing module that can be easily attached/detached to/from an air conditioner to wash containers contaminants such as dust and grease collecting in the heat exchanger of a system air conditioner.

In order to achieve the above objectives and other objects of the present disclosure, according to an embodiment of the present disclosure, a system for automatically washing and sterilizing a heat exchanger of a system air conditioner, which washes out contaminants such as dust, grease, mold, and bacteria collected on a cooling fin of a heat exchanger with a blowing fan separated from a fan motor, and sterilizes the cooling fin with an indoor unit installed or embedded in a ceiling panel, in a system air conditioner including the fan motor, the blowing fan, and the heat exchanger, includes:

a washer body including an air compressor that is mounted therein, a compressed air tank that is connected to the air compressor when air of the air compressor is insufficient, a detergent liquid tank, a detergent liquid-assistant heater, a washing water tank, a washing water-assistant heater, a high-pressure pump, a hot air generator, and a steam-heat generator;

a washing module including a motor protection cover that surrounds the fan motor, a driving motor that can rotate forward and backward within a predetermined angle range from an origin, a reducer that has an upper end fixed to a lower end of a fixing rod fixed to the motor protection cover, and is connected to the driving motor, and a spray nozzle that is mounted on a spray nozzle support connected to a rotary shaft of the reducer to be rotatable within a predetermined angle range from an origin, and selectively receives and sprays compressed air, detergent liquid, hot washing water, room-temperature washing water, steam, and hot air, which are supplied from the compressed air tank, the detergent liquid tank, the washing water tank, the hot water generator, the steam generator, and the hot air generator, to the cooling fin;

a waste water collection vinyl cover that has an upper opening fixed to the ceiling panel on which the air conditioner is mounted, is fixed at a portion of a bottom thereof to a lower end of a non-rotating hollow shaft, which is disposed through the rotary shaft of the reducer, not to sag, and collects contaminated waste water dropping when the cooling fin is washed by the spray nozzle; and a controller that controls the spray nozzle to selectively spray the compressed air, the detergent liquid, the hot washing water, the room-temperature washing water, and the steam, and the hot air to the cooling fin.

In order to achieve the above objects and other objects of the present disclosure, according to another embodiment of the present disclosure, a system for automatically washing and sterilizing a heat exchanger of a system air conditioner, which washes out contaminants such as dust, grease, mold, and bacteria collected on a cooling fin of a heat exchanger with a fan motor separated, and sterilizes the cooling fin with an indoor unit installed or embedded in a ceiling panel, in a system air conditioner including the fan motor, a blowing fan, and the heat exchanger, includes:

a washer body including an air compressor that is mounted therein, a compressed air tank that is connected to the air compressor when air of the air compressor is insufficient, a detergent liquid tank, a detergent liquid-assistant heater, a washing water tank, a washing water-assistant heater, a high-pressure pump, a hot air generator, and a steam-heat generator;

a washing module including one or more fixing rods having an upper end fixed to a fixing plate on which the fan motor is mounted, a driving motor that can rotate forward and backward within a predetermined angle range from an origin, and a spray nozzle that is mounted on a spray nozzle support rotatably connected to a rotary shaft of a reducer fixed to a lower end of the fixing rod and connected to the driving motor, and selectively receives and sprays compressed air, detergent liquid, hot washing water, room-temperature washing water, steam, and hot air, which are supplied from the compressed air tank, the detergent liquid tank, the washing water tank, the hot water generator, the steam generator, and the hot air generator, to the cooling fin;

a waste water collection vinyl cover that has an upper opening fixed to the ceiling panel on which the air conditioner is mounted, is fixed at a portion of a bottom thereof to a lower end of a non-rotating hollow shaft, which is disposed through the rotary shaft of the reducer, not to sag, and collects contaminated waste water dropping when the cooling fin is washed by the spray nozzle; and a controller that controls the spray nozzle to selectively spray the compressed air, the detergent liquid, the hot washing water, the room-temperature washing water, and the steam, and the hot air to the cooling fin.

In order to achieve the above objects and other objects of the present disclosure, according to another embodiment of the present disclosure, a module for washing an sterilizing a heat exchanger of a system air conditioner, which is designed to automatically wash out contaminants collected on a cooling fin of the heat exchanger with a blowing fan separated from a fan motor in the system air conditioner, and to sterilize the cooling fin, includes:

a metal housing that is detachably fixed to a shaft of the fan motor and has a fastening portion on a bottom thereof;

a motor protection cover that is fixed to a top of a flange of the housing to prevent detergent liquid or washing water, which is sprayed to wash the cooling fin, from flying to the fan motor;

a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a lower portion coupled to a reducer connected to the driving motor are disposed, and that is connected to a rotary shaft of the reducer to be rotated forward and backward by the driving motor;

a magnet that is formed on the fixing plate to temporarily fix the fixing plate by bringing the fixing plate in close contact with a bottom of the flange; and a fastening nut that is thread-fastened to a fastening portion disposed through a coupling hole of the fixing plate and detachably fixes the spray nozzle support to the housing.

In order to achieve the above objects and other objects of the present disclosure, according to another embodiment of the present disclosure, a module for washing an sterilizing a heat exchanger of a system air conditioner, which is designed to automatically wash out contaminants collected on a cooling fin of the heat exchanger with a blowing fan separated from a fan motor in the system air conditioner, and to sterilize the cooling fin, includes:

a housing that is detachably fixed to a shaft of the fan motor, that has a fastening portion protruding from a bottom thereof, and to which fastening bolts are fastened to face the bottom thereof with heads spaced apart from the bottom;

a motor protection cover that is fixed to a top of a flange of the housing to prevent detergent liquid or washing water, which is sprayed to wash the cooling fin, from flying to the fan motor;

a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a reducer connected to the driving motor are disposed, and that is connected to a rotary shaft of the reducer to be rotated forward and backward by the driving motor, in which oblong holes are formed in an arc shape to face each other in the fixing plate and the oblong holes are fitted on the fastening bolts so that the fixing plate is temporarily fixed to the heads without dropping from the housing when the fixing plate is swung at a predetermined angle; and a fastening nut that is thread-fastened to a fastening portion disposed through a coupling hole of the fixing plate and detachably fixes the spray nozzle support to the housing.

In order to achieve the above objects and other objects of the present disclosure, according to another embodiment of the present disclosure, a module for washing an sterilizing a heat exchanger of a system air conditioner, which is designed to automatically wash out contaminants collected on the cooling fin of a heat exchanger with a fan motor separated in a system air conditioner, and to sterilize the cooling fin, includes:

a fixing board mounted on a ceiling panel on which the heat exchanger is installed;

a metal housing detachably fixed to a bottom of the fixing board and having a fastening portion protruding from a bottom thereof;

a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a reducer connected to the driving motor are disposed, and that is connected to a rotary shaft of the reducer to be rotated forward and backward by the driving motor, a magnet that is formed on the fixing plate to temporarily fix the fixing plate by bringing the fixing plate in close contact with a bottom of the flange of the housing; and a fastening nut that is thread-fastened to a fastening portion disposed through a coupling hole of the fixing plate and detachably fixes the spray nozzle support to the housing.

In order to achieve the above objects and other objects of the present disclosure, according to another embodiment of the present disclosure, a module for washing an sterilizing a heat exchanger of a system air conditioner, which is designed to automatically wash out contaminants collected on the cooling fin of a heat exchanger with a fan motor separated in a system air conditioner, and to sterilize the cooling fin, includes:

a fixing board mounted on a ceiling panel on which the heat exchanger is installed;

a housing that is detachably fixed to a bottom of the fixing board, that has a fastening portion protruding from a bottom thereof, and to which fastening bolts are fastened to face the bottom thereof with heads spaced apart from the bottom;

a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a reducer are disposed, and that is connected to a rotary shaft of the reducer to be rotated forward and backward by the driving motor, in which oblong holes are formed in an arc shape to face each other in the fixing plate and the oblong holes are fitted on the fastening bolts so that the fixing plate is temporarily fixed to the heads without dropping from the housing when the fixing plate is swung at a predetermined angle; and a fastening nut that is thread-fastened to a fastening portion disposed through a coupling hole of the fixing plate and detachably fixes the spray nozzle support to the housing.

In order to achieve the above objects and other objects of the present disclosure, according to another embodiment of the present disclosure, a module for washing an sterilizing a heat exchanger of a system air conditioner, which is designed to automatically wash out contaminants collected on a cooling fin of the heat exchanger with a blowing fan separated from a fan motor in the system air conditioner, and to sterilize the cooling fin, includes:

a metal housing that has a band disposed at an upper portion thereof to surround an outer surface of the fan motor and fixed by a fastening member, has a lower portion detachably fixed by a fastening nut thread-fastened to a shaft of the fan motor disposed through a coupling hole of a bottom plate, and prevents washing water or detergent liquid sprayed when the cooling fin is washed from flying to the fan motor;

a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a reducer connected to the driving motor are disposed, and that is connected to a rotary shaft of the reducer to be rotated forward and backward by the driving motor, a magnet disposed on the fixing plate to fix the fixing plate by bringing a top of the fixing plate in close contact with a bottom of a flange of the housing.

In order to achieve the above objects and other objects of the present disclosure, according to another embodiment of the present disclosure, a module for washing an sterilizing a heat exchanger of a system air conditioner, which is designed to automatically wash out contaminants collected on a cooling fin of the heat exchanger with a blowing fan separated from a fan motor in the system air conditioner, and to sterilize the cooling fin, includes:

a housing that has a band disposed at an upper portion thereof to surround an outer surface of the fan motor and fixed by a fastening member, has a lower portion detachably fixed by a fastening nut thread-fastened to a shaft of the fan motor disposed through a coupling hole of a bottom plate, to which fastening bolts are fastened to face the bottom thereof with heads spaced apart from the bottom, and prevents washing water or detergent liquid sprayed when the cooling fin is washed from flying to the fan motor; and a spray nozzle support that has a spray nozzle mounted thereon to spray detergent liquid, steam, washing water, and hot air, which are selectively supplied through a first supply hose from the ground, to the cooling fin, inside which a driving motor rotating forward and backward and a fixing plate mounted on a fixing rod having a reducer connected to the driving motor are disposed, and that is connected to a rotary shaft of the reducer to be rotated forward and backward by the driving motor, in which oblong holes are formed in an arc shape to face each other in the fixing plate and the oblong holes are fitted on the fastening bolts so that the fixing plate is seated on the heads without dropping from the housing when the fixing plate is swung at a predetermined angle.

The system and module for automatically washing and sterilizing a heat exchanger of a system air conditioner having the configuration described above has the following advantages.

Since washing, rinsing, and drying are performed with dust, grease, mold, bacteria, etc., which are collected in a heat exchanger, swelling up, by spraying high-temperature washing water, a high-temperature detergent, high-temperature steam, and air (compressed air) heated at a high temperature from an air compressor with the exchange of an air conditioner installed, it is possible to considerably improve the efficiency of washing and sterilizing.

Since personnel expenses are reduced by minimizing man power for washing a heat exchanger, the economic burden on a user can be reduced.

A worker can easily detach/attach alone a washing module for washing out contaminants such as dust, mold, bacteria, grease, etc. collected in the heat exchange of a system air conditioner from/to the air conditioner.

Since contaminated washing water is collected when a heat exchanger installed in an office with a plurality of personal computers or a store with food is washed, it is possible to reduce the processes and time for washing and sterilizing.

Since the process of washing, sterilizing, and drying of a heat exchanger is stored as videos and the temperature and work time of each process is stored in real time into a graph, customers can directly check the internal state of an air conditioner before and after washing and sterilizing.

BRIEF DESCRIPTION OF THE DRAWINGS

The above and other objectives, features and other advantages of the present invention will be more clearly understood from the following detailed description when taken in conjunction with the accompanying drawings, in which.

DETAILED DESCRIPTION OF THE INVENTION

Figure 1:
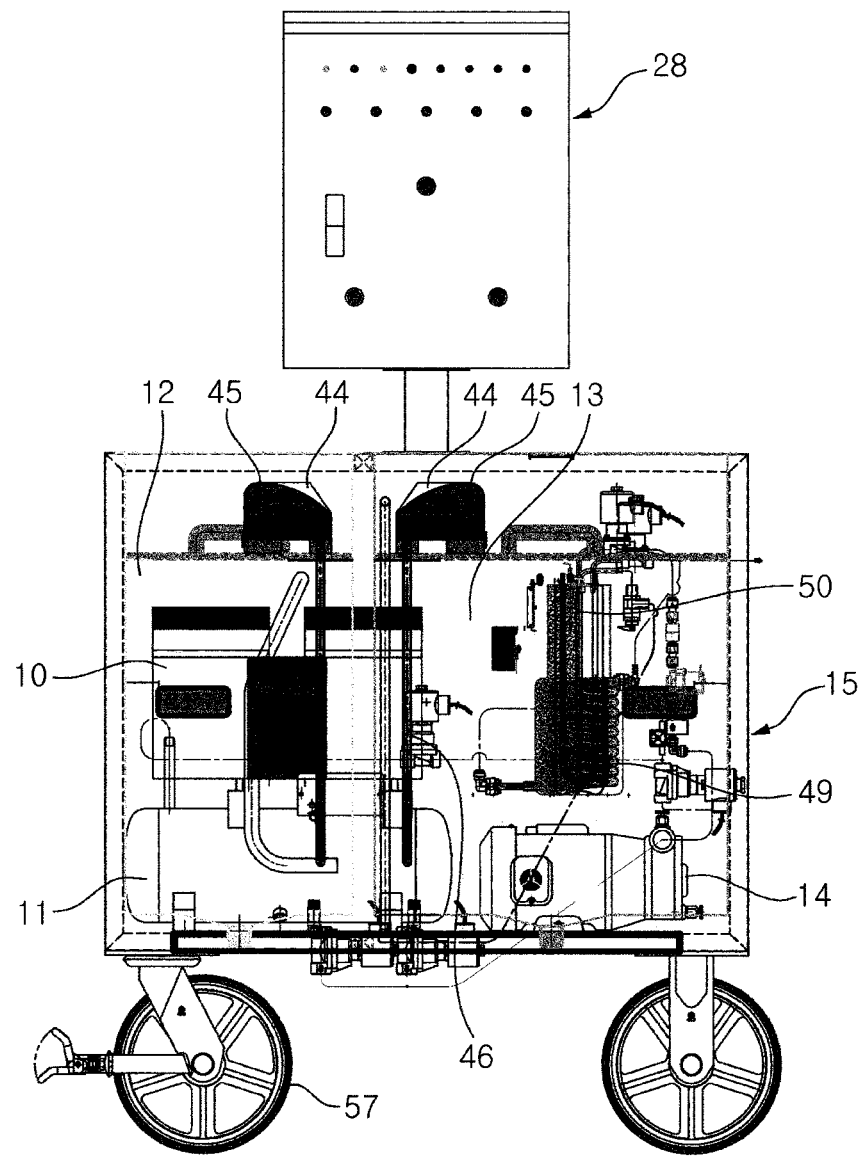
FIG. 1 is a schematic view of a system and module for automatically washing and sterilizing a heat exchanger of a system air conditioner according to an exemplary embodiment of the present disclosure.
Figure 2:
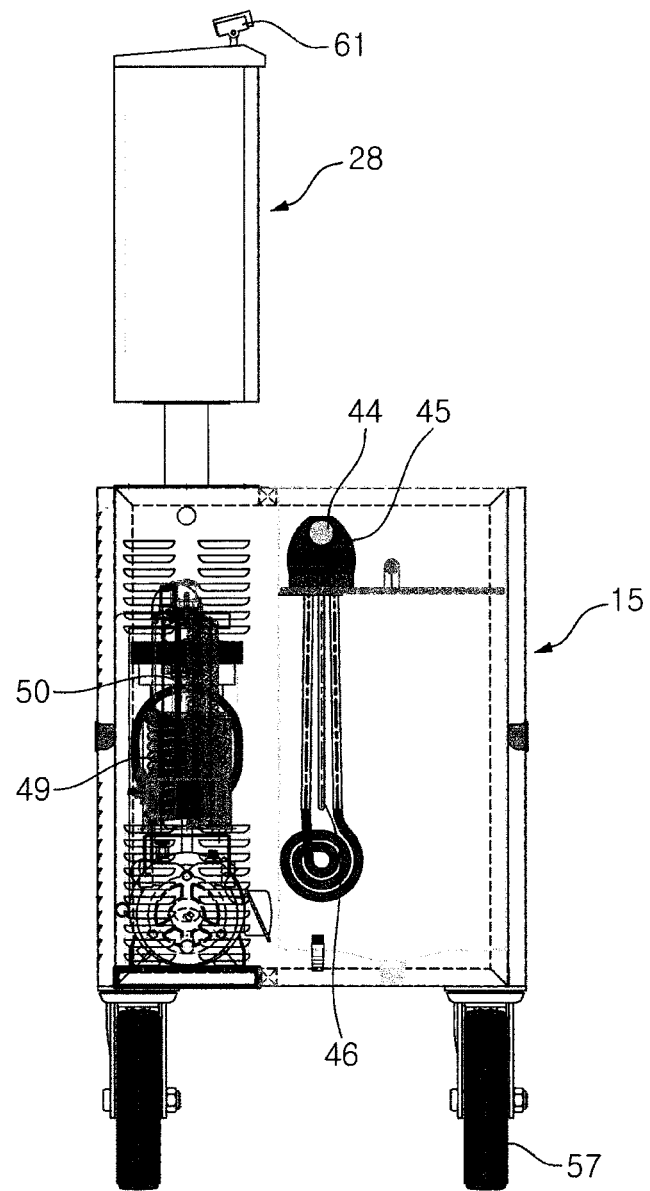
FIG. 2 is a side view of the washing and sterilizing system shown in FIG. 2.

Hereafter, a system air conditioner and, more particularly, a system and module for automatically washing and sterilizing a heat exchanger of a system air conditioner according to an exemplary embodiment of the present disclosure is described in detail with reference to the accompanying drawings.

Referring to FIGS. 1 to 11, a system and module for automatically washing and sterilizing a heat exchanger of a system air conditioner according to an embodiment of the present disclosure
is designed to wash out contaminants such as dust, grease, mold, and bacteria collected on a cooling fin of a heat exchanger with a blowing fan separated from a fan motor and sterilize the cooling fin with an indoor unit installed or embedded in a ceiling panel, in a system air conditioner (hereafter, referred to as an air conditioner) including the fan motor, the blowing fan, and the heat exchanger.

The system includes: a washer body 15 including an air compressor 10 that is mounted therein, a compressed air tank (functioning as an assistant air compressor) that is connected to the air compressor 10 when air (compressed air) of the air compressor 10 is insufficient, a detergent liquid tank 12, a detergent liquid-assistant heater 12-1, a washing water tank 13, a washing water-assistant heater 13-1, a high-pressure pump 14, a hot air generator 49, a steam-heat generator 50, and casters 57 being rotatably mounted on a floor;

a washing module including a motor protection cover 18 (having a bowl shape with an open top) that surrounds the fan motor 17 to be able to prevent washing water sprayed when the cooling fin 21 is washed from flying to the fan motor 17, one or more (e.g., three) fixing rods 58 that has an upper end mounted on the bottom of the motor protection cover 18 by a fixing bolt 54, a driving motor 20 that can be rotated forward and backward with a predetermined angle range from an origin, a spray nozzle support 19 that is connected to a rotary shaft 25 of a reducer 24, which is fixed to the lower end of the fixing rod 18 by a fixing bolt 60 and connected to the driving motor 20, to be rotatable forward and backward within a predetermined angle range, and one or more spray nozzles 22 that are mounted on the spray nozzle support 19 and selectively spray compressed air, detergent liquid, hot washing water, room-temperature washing water, steam & hot air, etc. which are supplied from the compressed air tank 11, the detergent air tank 12, the washing water tank 13, the hot air generator 49, the steam-heat generator 50, and the air compressor 10 to a cooling fin 21 for a first hot-water cleansing operation, a heat cleaning operation, a soaking-cleansing standby operation, a second hot-water cleansing operation, a room temperature water-cleansing operation, steam sterilization operation, and hot air-driving sterilizing operation;

a waste water collection vinyl cover 27 that has an upper opening fixed to the ceiling panel 53 on which the air conditioner 16 (the cooling fin 21 of the heat exchanger) is installed or embedded, is fixed at a portion of the bottom to the lower end of a non-rotating hollow shaft, which is disposed through a rotary shaft 25 of the reducer, not to sag, and collects contaminated waste water dropping when the cooling fin 21 is washed by the spray nozzles 22; and a controller 28 that controls the spray nozzles 22 to selectively spray the compressed air, detergent liquid, hot washing water, room-temperature washing water, and steam & hot air to the cooling fin 21.

The technique of storing compressed air produced by the air compressor 20 in the compressed air tank 11 is generally used in the time of filing of the present disclosure, so the configuration for this technique is not described in detail.

Further, the hot air generator 29 and the steam-heat generator 50 that generate hot air and steam at a predetermined temperature when power is supplied are also generally used in the field of the present disclosure, so they are not described in detail.

According to an exemplary embodiment, though not show in the figures, the operation of the washing module 23 is controlled to start and finish by operating any one of a notebook, a PC, a remote controller, and a control panel of the controller 28.

Figure 4:
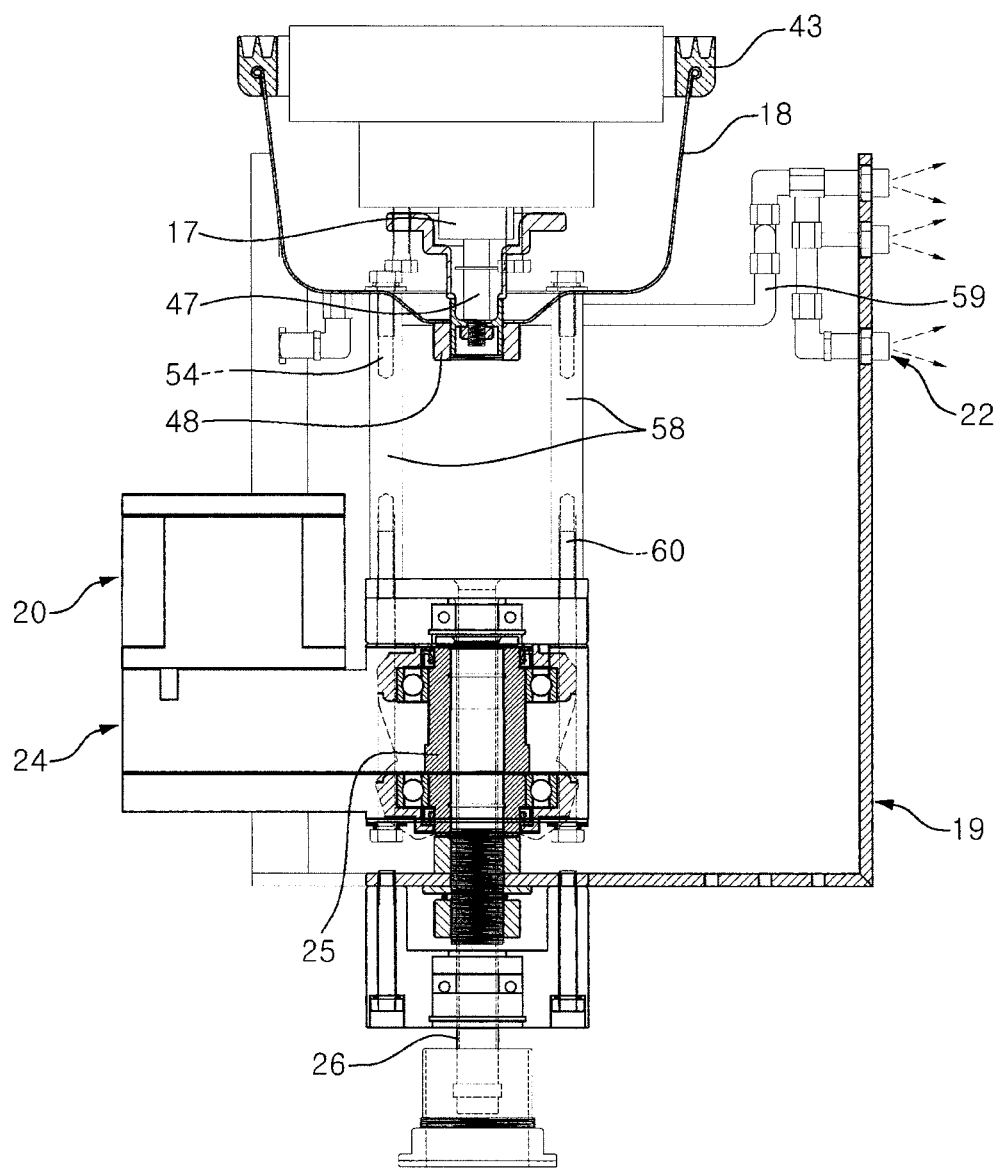
FIG. 4 is a schematic side view of the washing and sterilizing system shown in FIG. 1.
Figure 8:
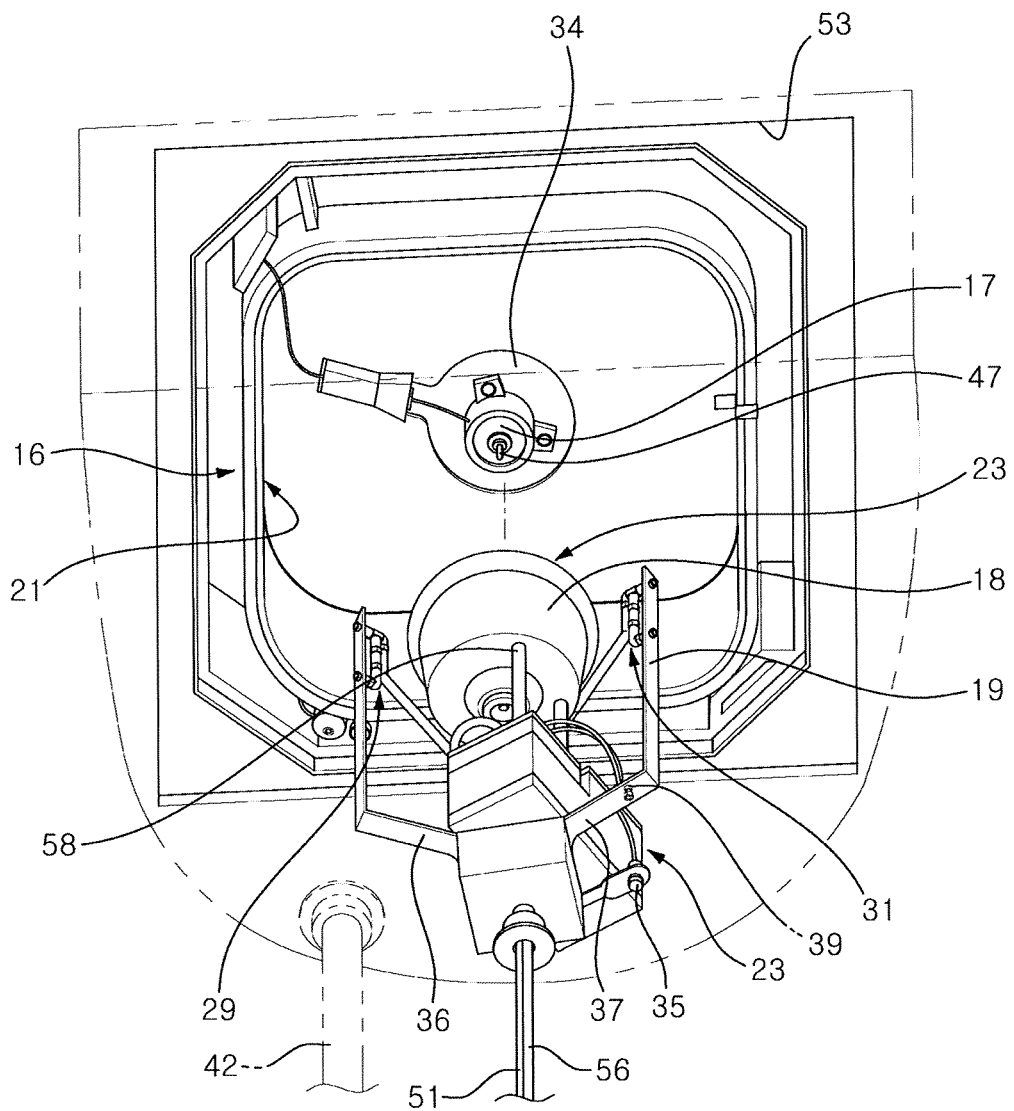
FIG. 8 is a view for describing that a washing module of the washing and sterilizing system shown in FIG. 1 is mounted on a fan motor of an air conditioner.
Figure 9:
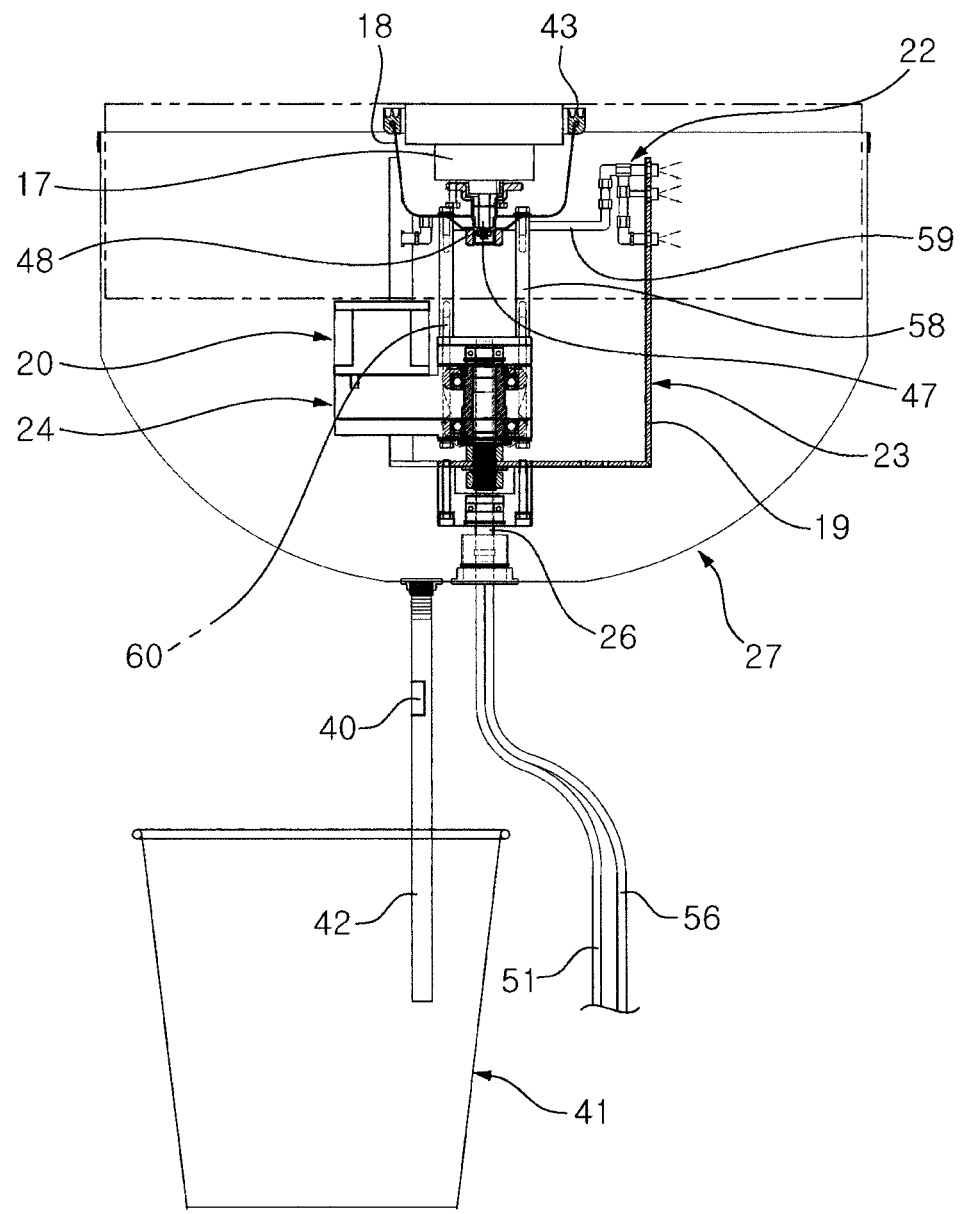
FIG. 9 is a view showing a use state of the system for automatically washing and sterilizing a heat exchanger of a system air conditioner shown in FIG. 1.

As shown in FIGS. 4, 8, and 9, the motor protection cover 18 is detachably fixed by a fixing nut 48 thread-fastened to a shaft 47 to which a blowing fan (not shown) of the air conditioner 16 is fixed.

As shown in FIGS. 4, 6, 7A, 7B, 8, 9, and 10, the washing module described above includes first, second, and third spray nozzles 29, 30, and 31 mounted on the spray nozzle support 19 having a tripod shape, and further includes: a first supply hose 51 (e.g., a high-temperature high-pressure hose or a silicon hose) for selectively supplying stem and hot air to the first, second, and third spray nozzles 29, 30, and 31; and a second supply hose 52 (e.g., a high-temperature high-pressure hose or a silicon hose) for selectively supplying hot water, hot detergent liquid, and room-temperature washing water to the first, second, and third spray nozzles 29, 30, and 31.

Figure 5:
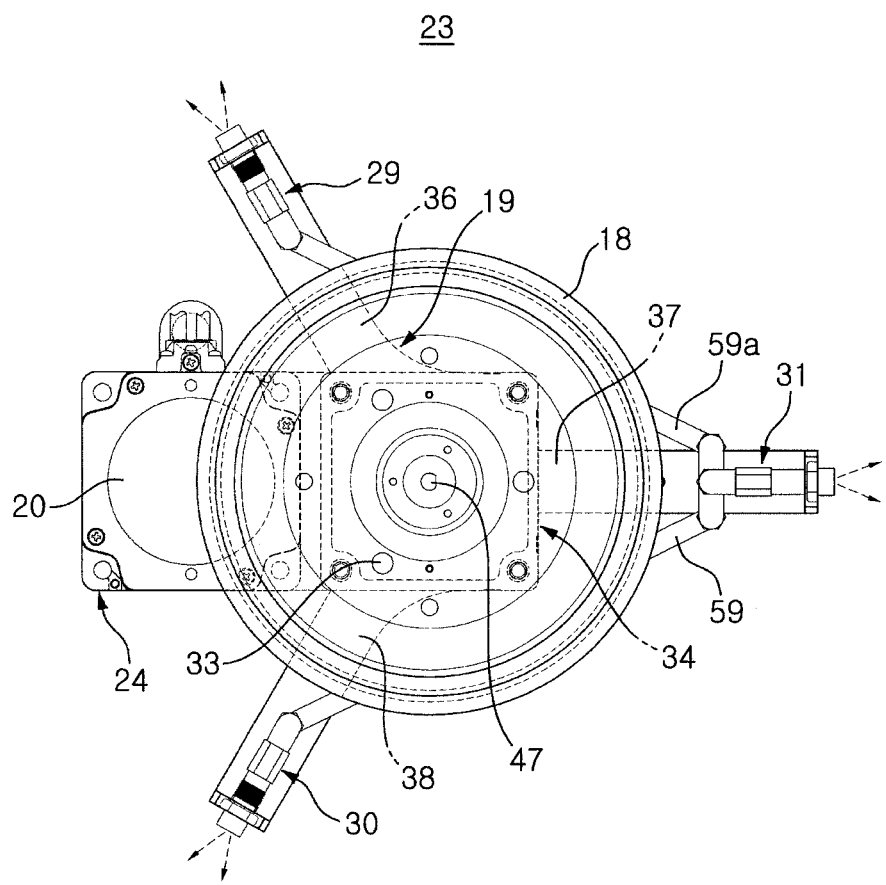
FIG. 5 is a plan view of the washing and sterilizing system shown in FIG. 4.
Figure 6:
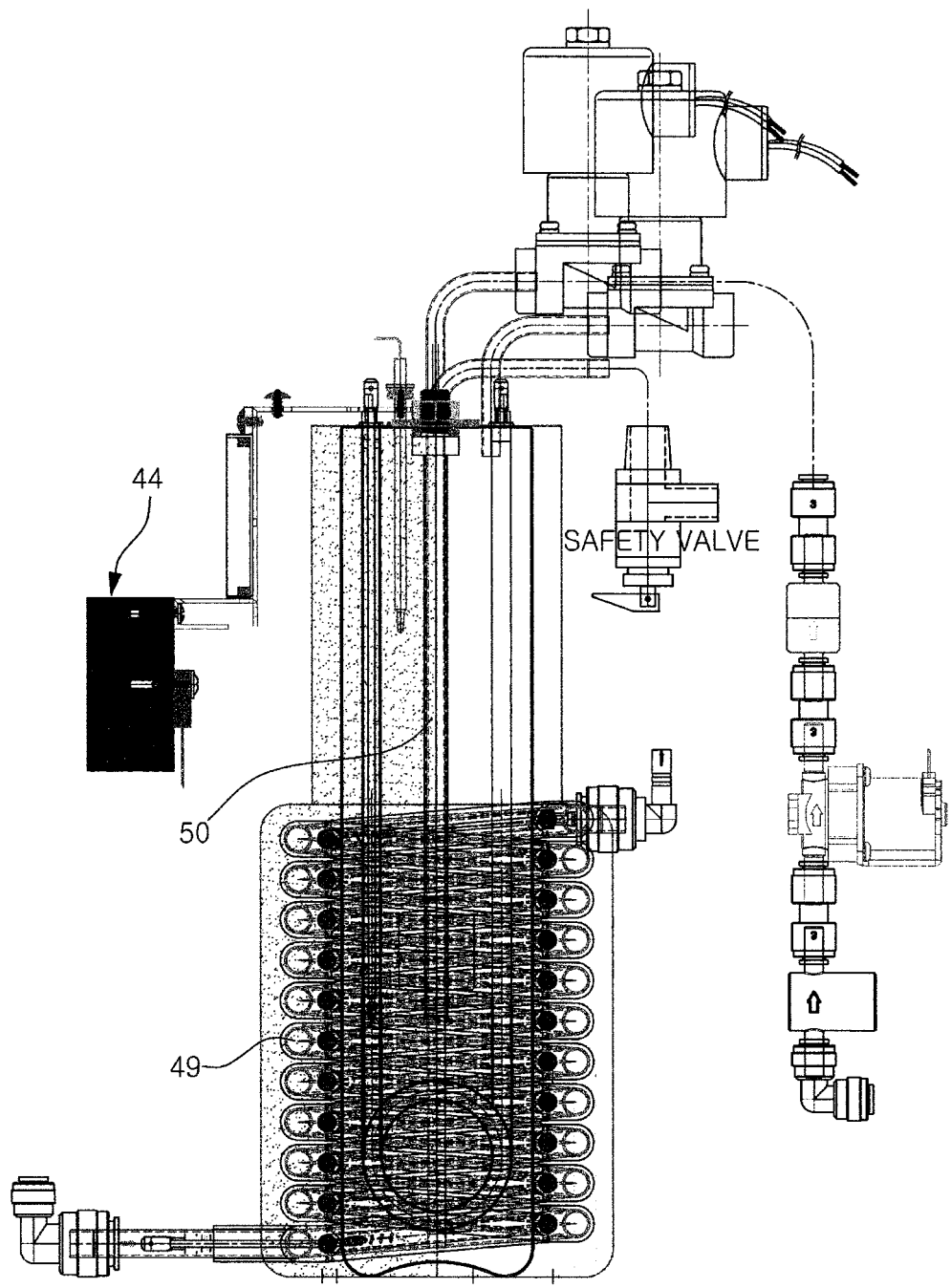
FIG. 6 is a view showing a heat generator and a steam generator of the washing and sterilizing system shown in FIG. 1.

As shown in FIGS. 4, 5, and 9, the washing module 23 described above further includes an anti-rotation fixing bolt 33 formed on the bottom inside the motor protection cover 18 and having an end supported on the bottom of a fixing plate 34 of the fan motor 17 through a thread-fastened fixing nut 32 to be able to prevent the motor protection cover 18 from being rotated by torque of the spray nozzle support 19 repeatedly rotating forward and backward within a predetermined angle range when the washing module 23 washes and sterilizes the cooling fin 21.

Figure 7A:
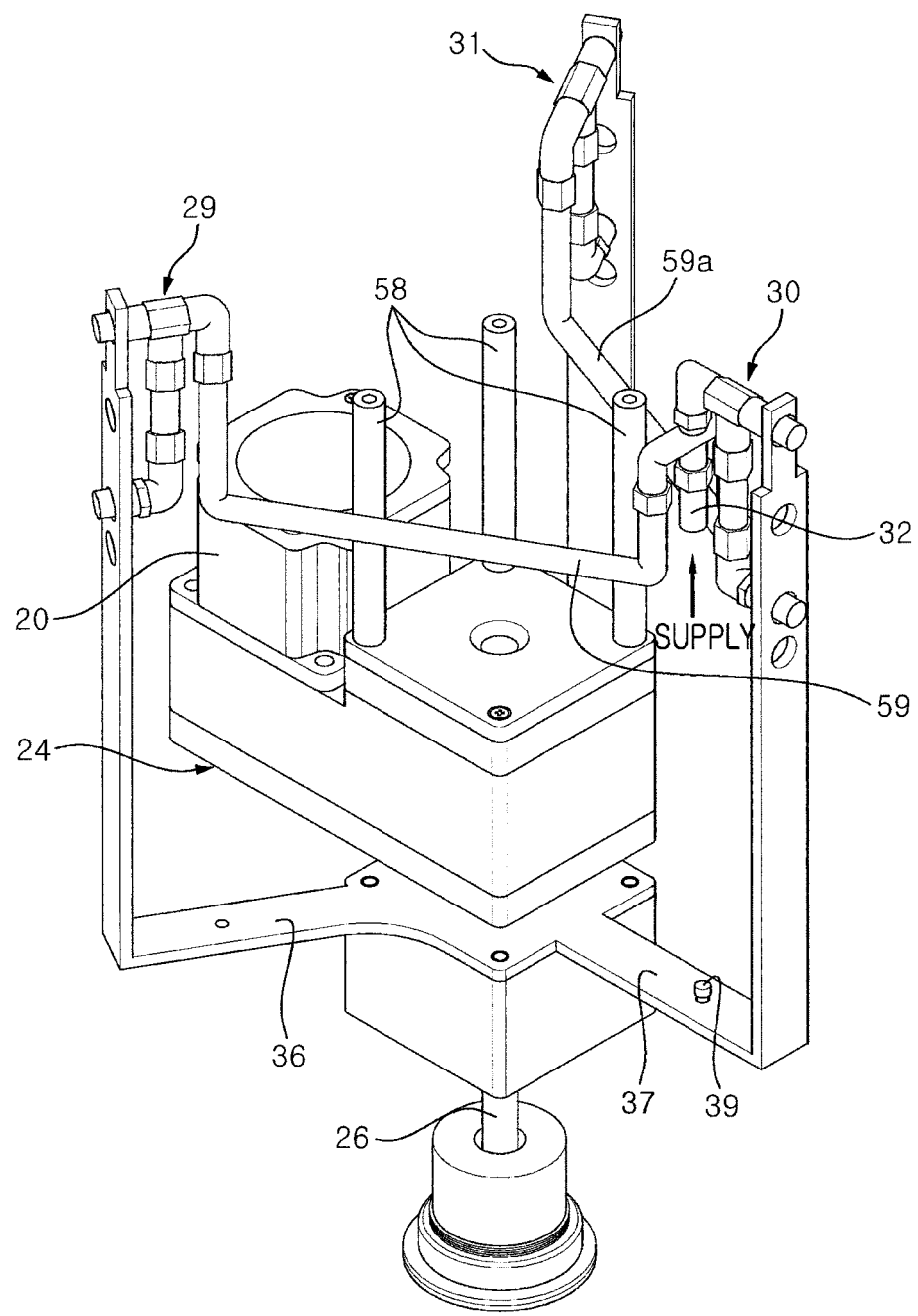
FIGS. 7A and 7B are views showing a washing module of the washing and sterilizing system shown in FIG. 1.
Figure 7B:
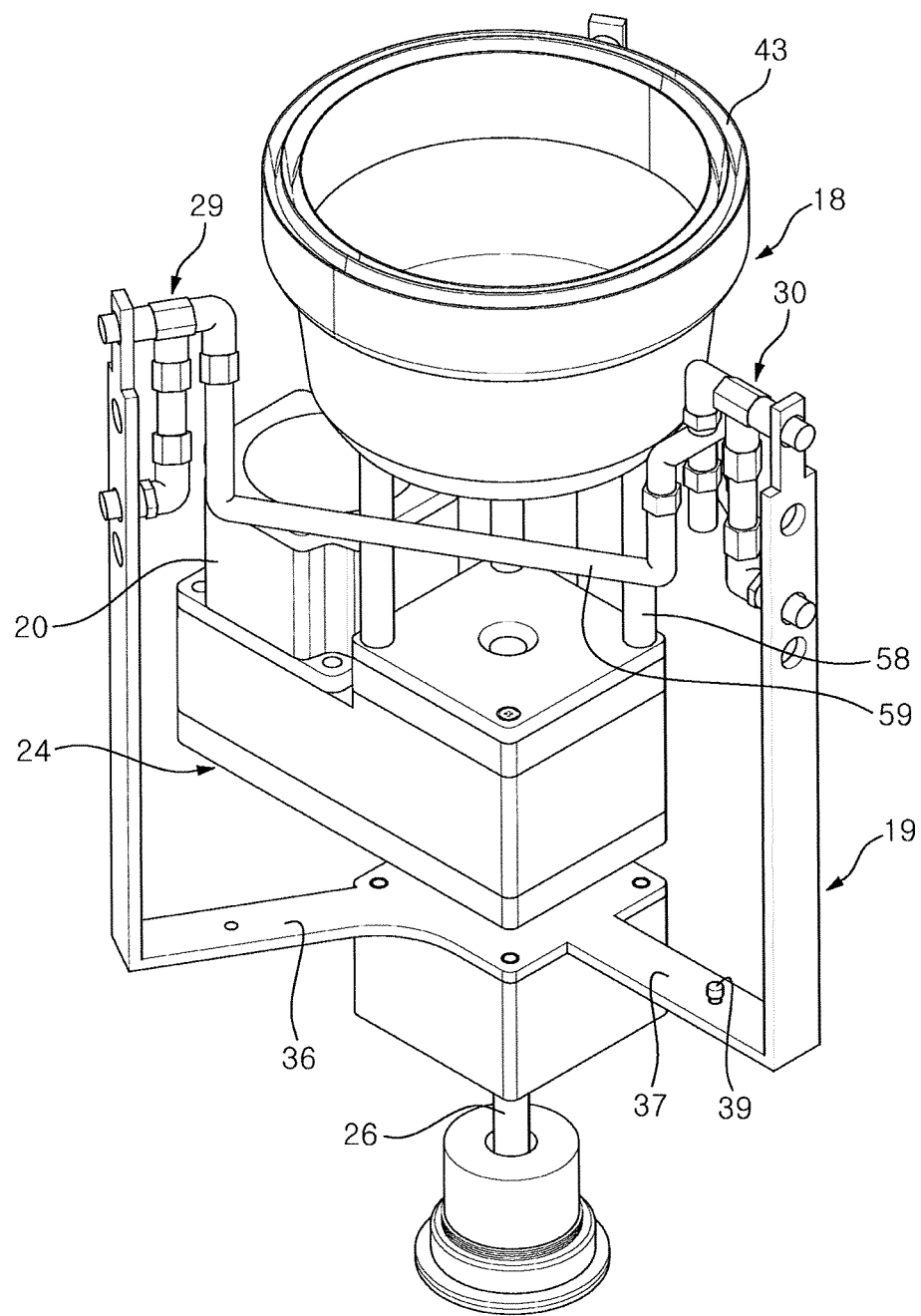

As shown in FIGS. 7A, 7B, and 8, the washing module 23 described above further includes: a proximity sensor 35 mounted on the bottom of the reducer 23 connected to the driving motor 20; and a pair of origin pointers 39 mounted on the tops of adjacent horizontal members 37 and 38 of three horizontal members 36, 37, and 38 maintaining 120 degrees of the spray nozzle support 19 to be positioned within a predetermined distance set with respect to the proximity sensor 35 when the spray nozzle support 19 is rotated.

When the spray nozzle support 19 is rotated and the origin pointers 39 are sensed by the proximity sensor 35, the rotation direction of the spray nozzle support 19 that is rotated forward and backward within a predetermined angle range by the driving motor 20 is changed.

The waste water collection vinyl cover 27 described above is made of a transparent material so that it is possible to visually check the process of washing the cooling fin 21 using the washing module 23 or to take a picture using a camera mounted on a camera support 61 of the controller 15.

As shown in FIG. 9, the waste water collection vinyl cover 27 described above further has: a drain 40 formed in the bottom of the waste water collection vinyl cover 27 described above; and a drain pipe 42 for discharging waste water collected in the waste water collection vinyl cover 27 described above to a waste water storage container 41 on the floor (ground).

As shown in FIGS. 4 and 9, the motor protection cover 18 described above further includes a packing 43 disposed on the edge of the top opening of the motor protection cover 18 and fixed to a fixing plate 34 of the fan motor 17 of the air conditioner 16 to prevent washing water or cleansing liquid, which is sprayed to wash and sterilize the cooling fin 21 by the washing module 23, from flying to the fan motor 17.

As shown in FIG. 1, the detergent liquid tank 12 described above and the washing water tank 13 further include an assistant heater 45 equipped with a temperature adjuster 33, and a temperature sensor 46.

In the drawings, reference numeral '46' indicates the camera support on which a camera (not shown) taking and storing pictures before and after the process of washing the cooling fin 21 described above by the washing module 23 to be able to provide data and videos to customers.

Reference numeral '32' indicates a connector for distributing and supplying washing water, steam, etc., which are selectively supplied through the first supply hose 51 or the second supply hose 52, to the spray nozzles 29, 30, and 31 through distribution pipes 59 and 59*a*.

Hereafter, an example of using the system for automatically washing and sterilizing a heat exchanger of a system air conditioner according to an embodiment of the present disclosure is described with reference to the accompanying drawings.

As shown in FIGS. 1 to 11, a blowing fan of the system air conditioner 16 that is embedded in the ceiling of a building is separated from the fan motor 17 and then the motor protection cover 18 is fixed to the fixing nut 48 thread-fastened to the shaft 47 of the fan motor 17.

The upper end of the spray nozzle support 19 is fastened to the bottom of the motor protection cover 18 by the fixing bolt 54.

The work of fixing the spray nozzle support 19 described above to the motor protection cover 18 using the fixing bolt is performed earlier than the work of fixing the motor protection cover 18 to the shaft 47 of the fan motor 17 using the fixing nut 48.

The top opening of the waste water collection vinyl cover 27 for collecting waste water contaminated when the cooling fin 21 is washed by the spray nozzle 22 is fixed to the ceiling panel 53 on which the air conditioner 16 is installed.

Accordingly, when the driving motor 20 is operated in response to a control signal from the controller and the spray nozzle support 19 is repeatedly rotated forward and backward in a predetermined angle range, contaminants (dust, grease, mold, bacteria, etc.) sticking to the cooling fin 21 of the system air conditioner 16 can be washed out and the cooling fin 21 can be sterilized and dried by the first hot-water cleansing operation, a heat cleaning operation, a soaking-cleansing standby operation, a second hot-water cleansing operation, a room temperature water-cleansing operation, steam sterilization operation, and hot air-driving sterilizing operation through the spray nozzle 22 mounted on the tripod-shaped spray nozzle support 19.

Figure 3A:
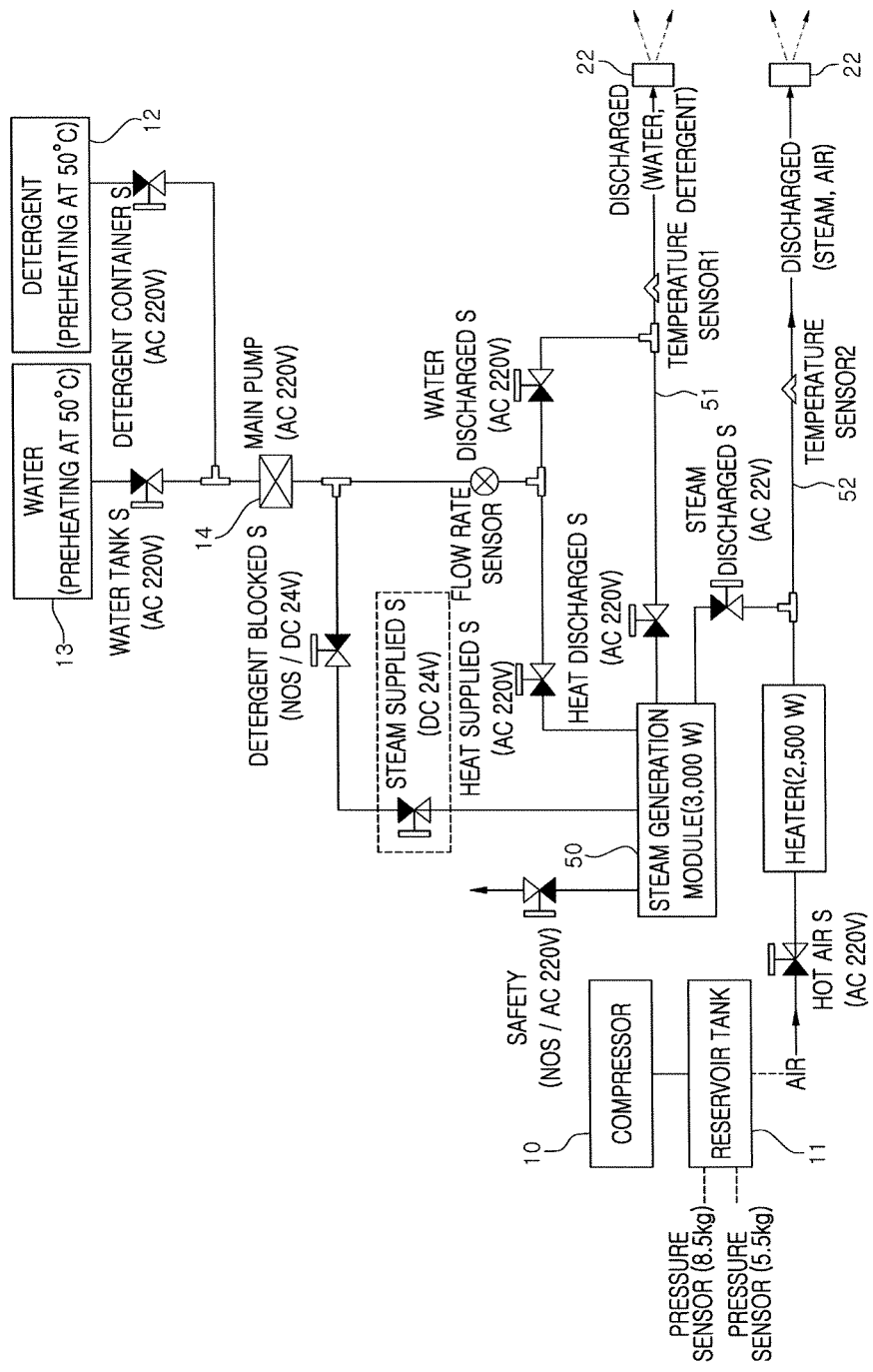
FIGS. 3A to 3C are views for describing supply of washing water, cleansing liquid, and air pressure that are supply by a controller of the washing and sterilizing system shown in FIG. 1.
Figure 3B:
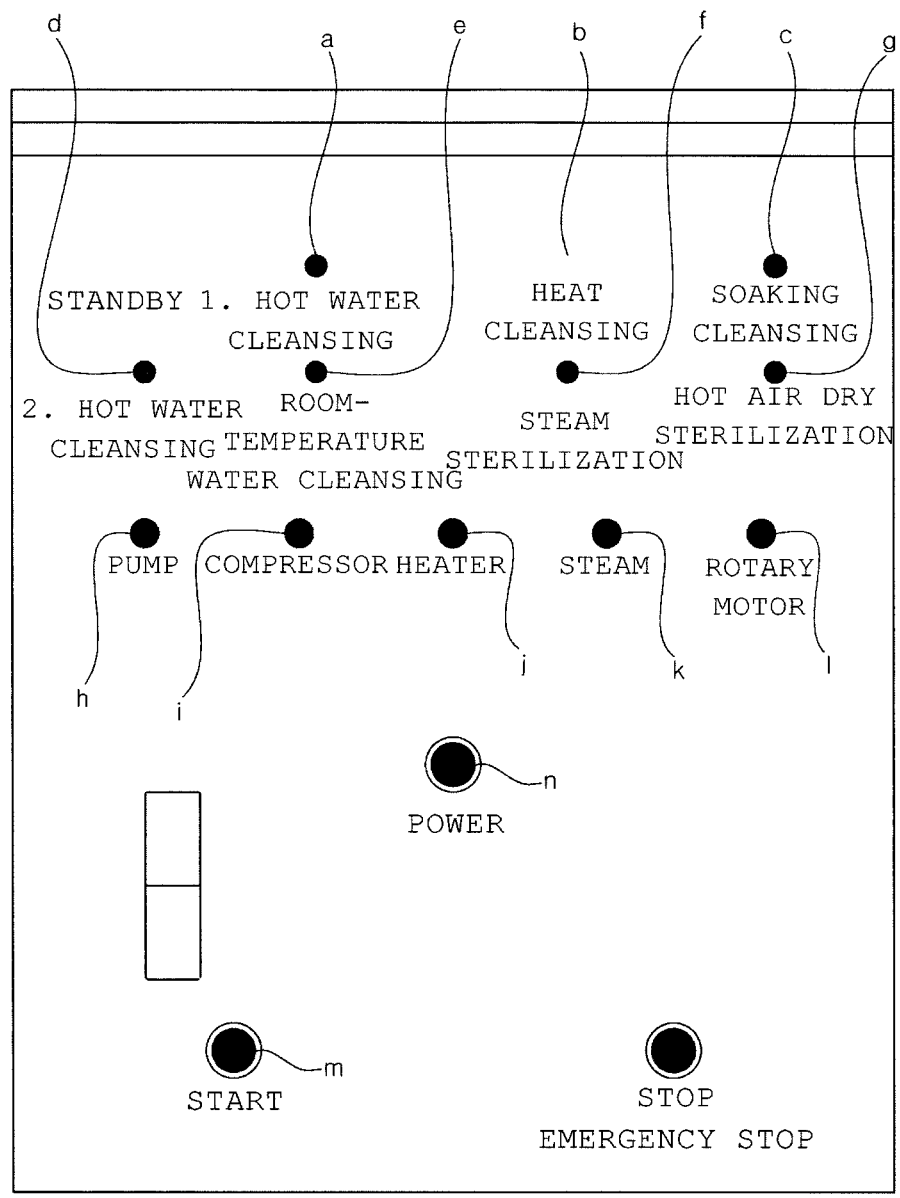
Figure 11:
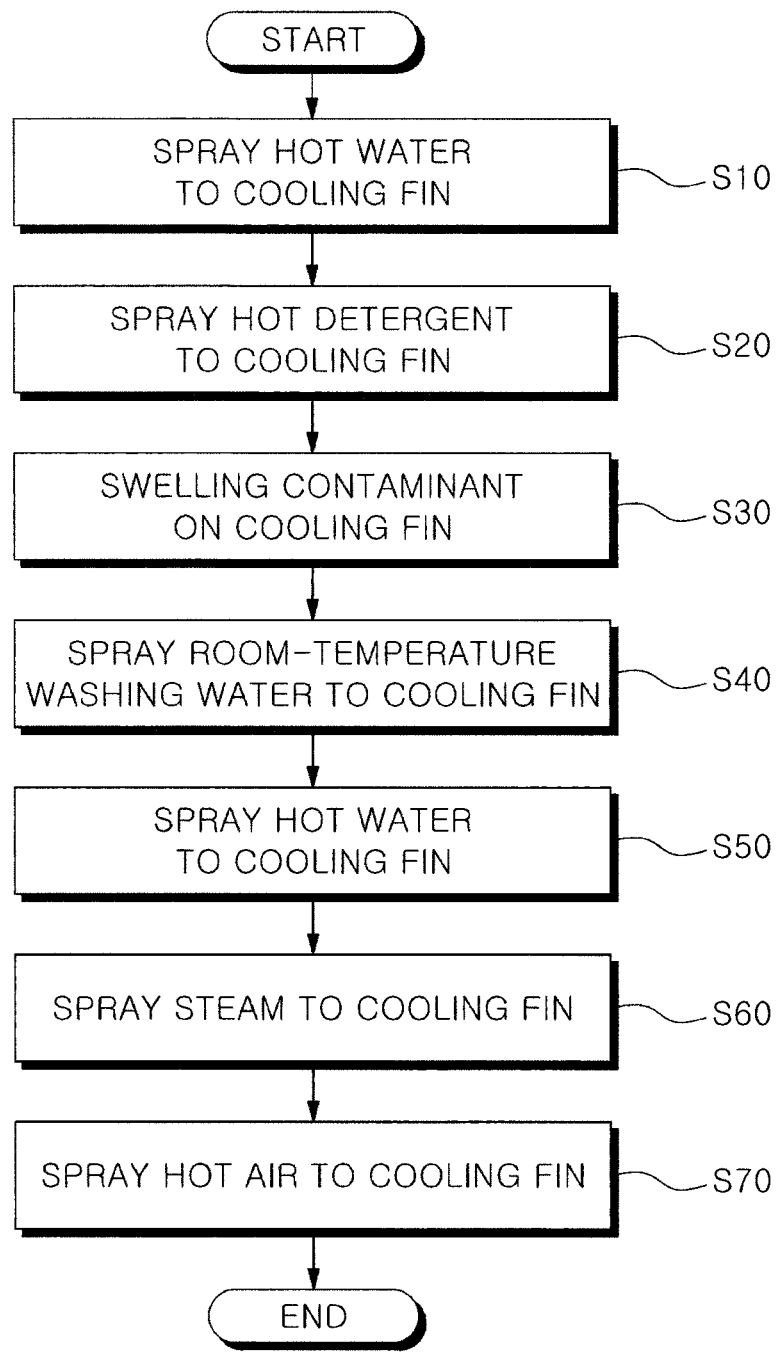
FIG. 11 is a flowchart showing a process of washing a cooling fin using the system for automatically washing and sterilizing a heat exchanger of a system air conditioner shown in FIG. 1.

In detail, as shown in FIG. 3B and in S10 of FIG. 11, when a worker touches a start button 'm' of the controller 28, work of washing out contaminants sticking to the cooling fin 21 and sterilizing the cooling fin is started. In this case, a standby LED turned on in a standby state is turned off.

Room-temperature washing water from the washing water tank 13 described above flows through a high-pressure pump 14 (a pump LED 'h' is turned off when the high-pressure pump is operated) and the hot air generator 49 of a steam generation module (maintained at about 95° C.), whereby high-temperature hot water at a predetermined temperature flows through the first supply hose 51 and is sprayed to the cooling fin 21 through the spray nozzles 29, 30, and 31 mounted on the spray nozzle support 19 (i.e., which is a primary hot-water washing operation).

The tripod-shaped spray nozzle support 19 connected to the driving motor 20 described above (a rotary motor LED 'l' is turned off when the driving motor is operated) can be repeatedly rotated forward and backward a predetermined number of times within a predetermined angle range. In this case, a first hot-water cleansing LED 'a' is turned off and is then turned on when the operation is finished.

That is, when the tripod-shaped spray nozzle support 19 is rotated forward (clockwise) within a predetermined angle range by the driving motor 20 and any one of the origin pointers 39 mounted on adjacent horizontal members 37 and 38 of the three horizontal members 36, 37, and 38 (maintaining 120 degrees) constituting the spray nozzle support 19 is moved within a predetermined distance and sensed by the proximity sensor 35 mounted on the outer surface of the reducer 24, a detection signal is provided to a driving unit of the driving motor 20.

Accordingly, when the rotation direction of the driving motor 20 is reversed (counterclockwise), the spray nozzle support 19 is rotated backward within a predetermined angle range.

That is, the spray nozzle support 19 can be repeatedly rotated forward and backward to predetermined angle by a predetermined number of times by the proximity sensor 35 sensing the origin pointers 39.

Even though the spray nozzle support 19 is repeatedly rotated forward and backward within a predetermined angle range to rotate the spray nozzle 22 described above, twisting of the first supply hose 51 and a power cable 56 for supplying power to the driving motor 20 can be prevented.

That is, the first supply hose 51 and the power cable 56 pass through the rotary shaft 25 of the reducer and pass through the non-rotating pipe-shaped hollow shaft 26, so twisting of the first supply hose 51 and the power cable 56 can be prevented when the spray nozzle 22 is rotated.

As shown in FIG. 3B and in S20 of FIG. 11, hot detergent liquid is supplied from the detergent liquid tank 12 through the first supply hose 51 by the high-pressure pump 14 (the LED 'h' is turned off when the high-pressure pump is operated) and is then sprayed to the cooling fin 21 through the spray nozzles 29, 30, and 31 mounted on the spray nozzle support 19 rotating forward and backward a predetermined number of times. In this case, a hot detergent LED 'b' is turned off and is then turned on when the operation is finished.

As shown in FIG. 3B and in S30 of FIG. 11, the contaminants sticking in a solid state to the cooling fan 21 can swell up when a predetermined time passes after the hot detergent liquid is sprayed to the cooling fin 21 by the spray nozzle 22 described above. In this case, a soaking-cleansing LED 'c' is turned off and is then turned on when the operation is finished.

As shown in FIG. 3B and in S40 of FIG. 11, when room-temperature washing water is pumped up from the washing water tank 13 described above to pass through the steam-heat generator 50 (at 138° C.) by the high-pressure pump 14 (a pump LED 'h' is turned off when the high-pressure pump is operated), high-temperature hot water at a predetermined temperature (maintained at about 95° C.) flows through the first supply hose 51 and is then sprayed to the cooling fin 21 through the spray nozzle 29, 30, and 31 mounted on the spray nozzle support 19 rotating forward and backward a predetermined number of times (i.e., which is a secondary hot-water cleansing operation). In this case, a room temperature water-cleansing LED 'e' is turned off and is then turned on when the operation is finished.

Accordingly, the contaminants sticking to the cooling fin 21 can further swell up.

As shown in FIG. 3B and in S50 of FIG. 11, hog water is supplied from the washing water tank 13 through the first supply hose 51 by the high-pressure pump 14 (the LED 'h' is turned off when the high-pressure pump is operated) and is then sprayed to the cooling fin 21 through the spray nozzles 29, 30, and 31 mounted on the spray nozzle support 19 rotating forward and backward a predetermined number of times, whereby the contaminants sticking to the cooling fin 21 and swelling up thereon can be removed. In this case, a hot water cleansing LED 'd' is turned off and is then turned on when the operation is finished.

As shown in FIG. 3B and in S60 of FIG. 11, when room-temperature washing water is pumped up from the washing water tank 13 described above to pass through the steam-heat generator 50 (a steam LED 'k' is turned off when the heat generator is operated) by the high-pressure pump 14 (a pump LED 'h' is turned off when the high-pressure pump is operated), steam at a predetermined temperature (maintained at about 138° C.) flows through the second supply hose 52 and then can be sprayed to the cooling fin 21 through the spray nozzle 29, 30, and 31 mounted on the spray nozzle support 19 rotating forward and backward a predetermined number of times.

Accordingly, mold, bacteria, etc. sticking to the cooling fin 21 can be removed. In this case, a first hot-water cleansing LED 'a' is turned off and is then turned on when the operation is finished. In this case, a steam cleansing LED 'f' is turned off and is then turned on when the operation is finished.

As shown in FIG. 3B and in S70 of FIG. 11, while compressed air from the compressed air tank 11 described above (a compressor LED 'i' is turned off when the compressed air tank is operated) flows through the double-pipe hot air generator 49 having a heater therein, air heated by the heater flows along the second supply hose 52 and is discharged to the cooling fin 21 to dry the cooling fin 21 through the spray nozzle 29, 30, and 31 mounted on the spray nozzle support 19 rotating forward and backward a predetermined number of times, whereby the moisture of the washing water or the cleansing liquid remaining on the cooling fin 21 is removed. Accordingly, propagation of mold, bacteria, etc. can be prevented. In this case, a hot air cleansing LED 'g' is turned off and is then turned on when the operation is finished.

Figure 10:
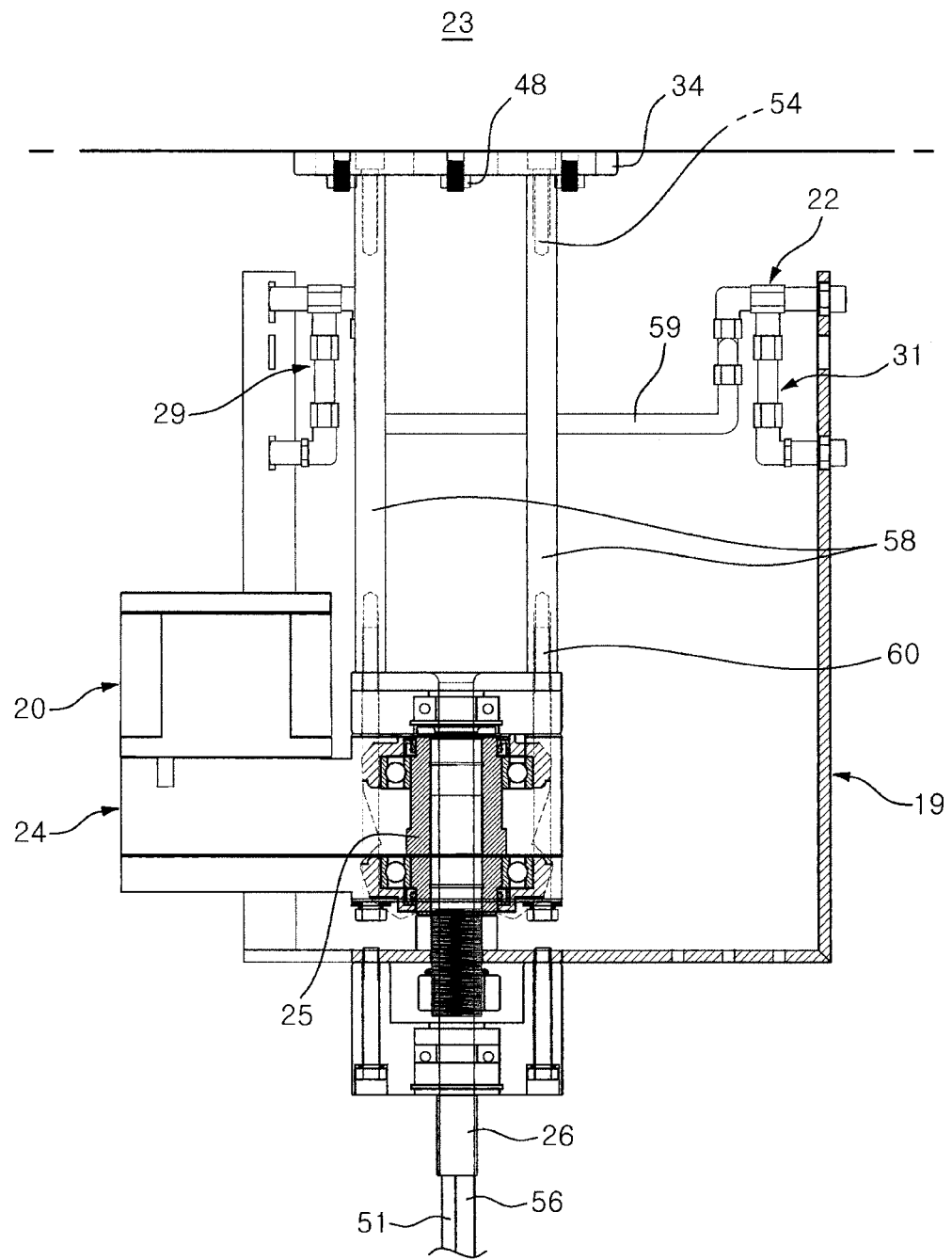
FIG. 10 is a view for describing that a washing module for washing a cooling fin of a heat exchanger of the washing and sterilizing system shown in FIG. 1 is mounted with a fan motor of an air conditioner separated.

Referring to FIGS. 10 to 11, a system and module for automatically washing and sterilizing a heat exchanger of a system air conditioner according to another embodiment of the present disclosure is designed to wash out contaminants such as dust, grease, mold, and bacteria collected on cooling fins of a heat exchanger with a fan motor having a blowing fan separated and sterilize the cooling fin with an indoor unit installed or embedded in a ceiling panel, in a system air conditioner including the fan motor, the blowing fan, and the heat exchanger.

The system includes: a washer body 15 including an air compressor 10 mounted therein, a compressed air tank 11 connected to the air compressor 10 when air of the air compressor 10 is insufficient, a detergent liquid tank 12, a detergent liquid-assistant heater 12-1, a washing water tank 13, a washing water-assistant heater 13-1, a high-pressure pump 14, a hot air generator 49, a steam-heat generator 50, and a caster 57 being rotatably mounted on a floor;

a washing module 23 including a fixing plate 32 on which a fan motor is mounted, one or more (e.g., three) fixing rods 58 that have an upper end fixed by a fixing bolt 54 fixed to the fixing plate 34, a driving motor 20 that can rotate forward and backward within a predetermined angle range from an origin, a spray nozzle support 19 that is connected to a rotary shaft 25 of a reducer 24, which is fixed to the lower end of the fixing rod 58 by a fixing bolt 60 and connected to the driving motor 20, to be rotatable within a predetermined angle range, and one or more spray nozzles 22 that are mounted on the spray nozzle support 19 and selectively receive and spray hot compressed air, detergent liquid, and washing water, which are supplied from the compressed air tank 11, the detergent liquid tank 12, the washing water tank 13, the steam-heat generator 50, and the hot air generator 49, to the cooling fin;

a waste water collection vinyl cover 27 that has an upper opening fixed to the ceiling panel 53 on which the air conditioner 16 (the cooling fins 21 of the heat exchanger) is installed or embedded, is fixed at a portion of the bottom to the lower end of a non-rotating hollow shaft, which is disposed through a rotary shaft 25 of the reducer, not to sag, and collects waste water dropping when the cooling fins 21 are washed by the spray nozzles 22; and a controller 28 that controls the spray nozzles 22 to selectively spray the hot compressed air, the detergent liquid, and the washing water to the cooling fin 21 sequentially in accordance with programs such as a first hot-water cleansing operation, a heat cleaning operation, a soaking-cleansing standby operation, a second hot-water cleansing operation, a room temperature water-cleansing operation, steam sterilization operation, and hot air-driving sterilizing operation.

Since the configuration except for the spray nozzle support 19 detachably mounted on the fixing plate 34 to which the fan motor 27 is fixed by the fixing bolt 54 (i.e., in which the motor protection cover 18 for protecting the fan motor 17 from flying washing water when the washing water is sprayed by the spray nozzles 22 to wash the cooling fin 21 is not used) is substantially the same as the system for automatically washing and sterilizing a heat exchanger of a system air conditioner according to an embodiment of the present disclosure, the configuration is not described and repeated reference numerals indicate parts having the same function.

Figure 3C:
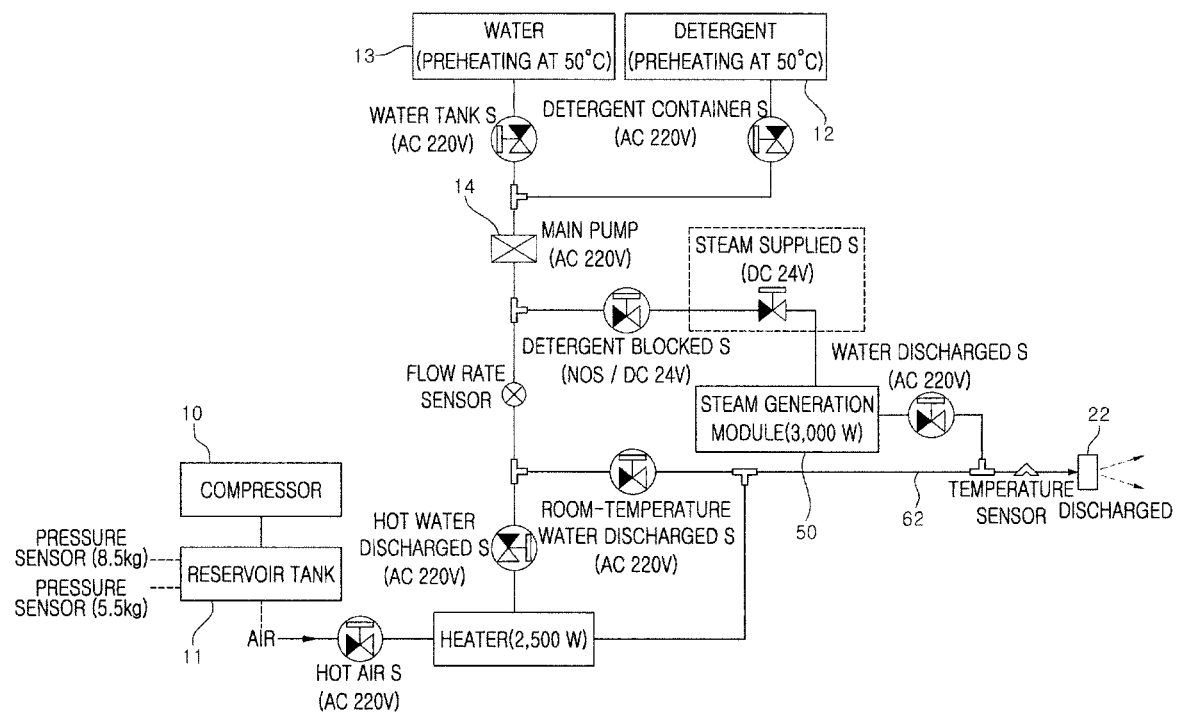

As shown in FIGS. 1 and 3C, the spray nozzle 22 of the washing module 23 described above may be provided as one or more pieces to be mounted on the spray nozzle support 19 connected to the driving motor 20 being able to rotate forward and backward within a predetermined angle range, and to selectively receive and spray hot compressed air, detergent liquid, and washing water, which are supplied from the compressed air tank 11, the detergent liquid tank 12, the washing water tank 13, the steam-heat generator 50, and the hot air generator 49, to the cooling fin 21 through a third supply hose 62.

For example, though not shown in the figures, when two spray nozzles 22 are mounted on the spray nozzle support 19 with a gap of 190 degrees to face each other, the spray nozzles 22 are repeatedly rotated to about 190 degrees to the left and about 190 degrees to the right by a predetermined number of times by the driving motor 20 rotating forward and backward.

Figure 12:
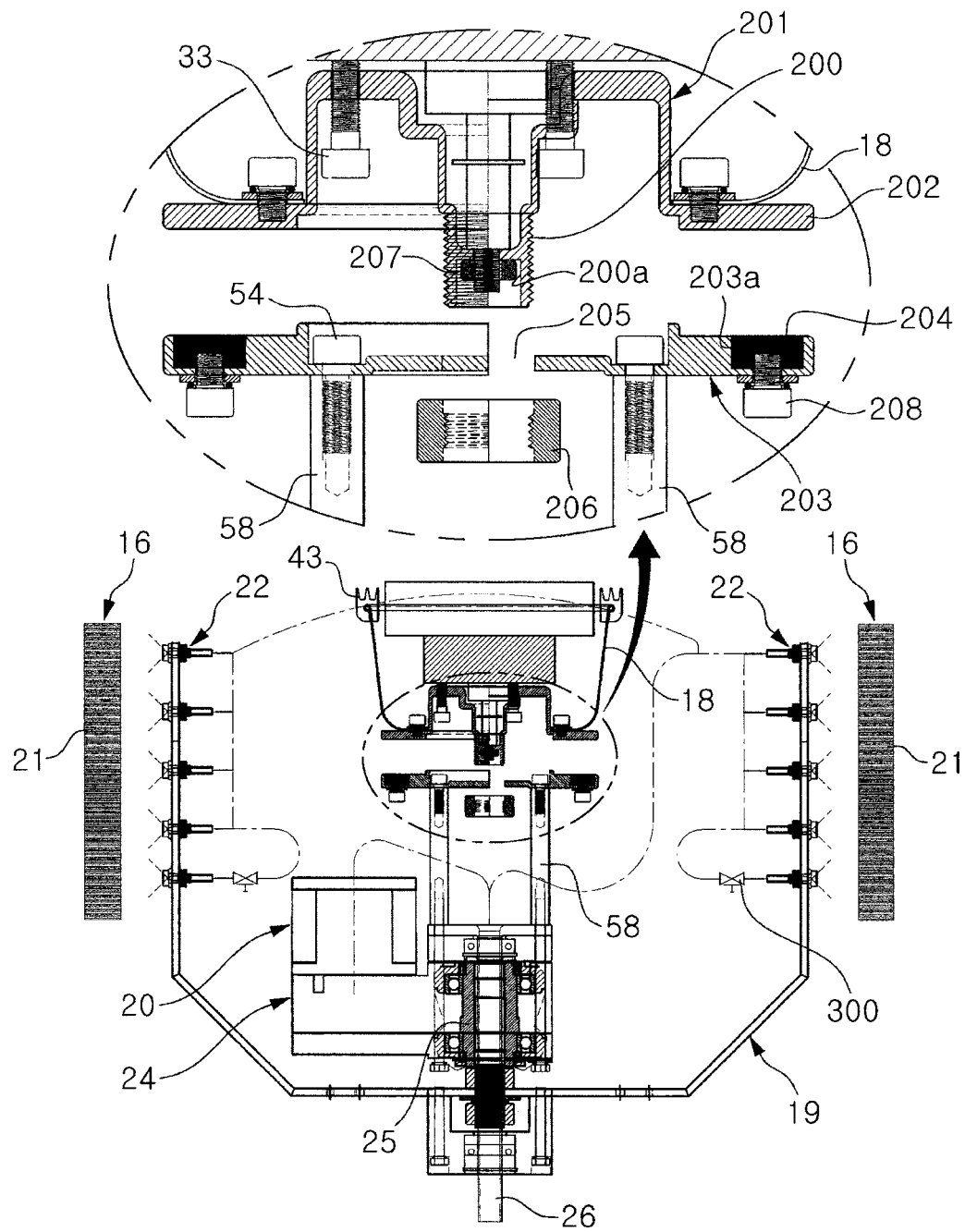
FIG. 12 is a cross-sectional view showing main parts of a module for washing and sterilizing a heat exchanger of a system air conditioner according to an exemplary embodiment of the present disclosure.
Figure 13:
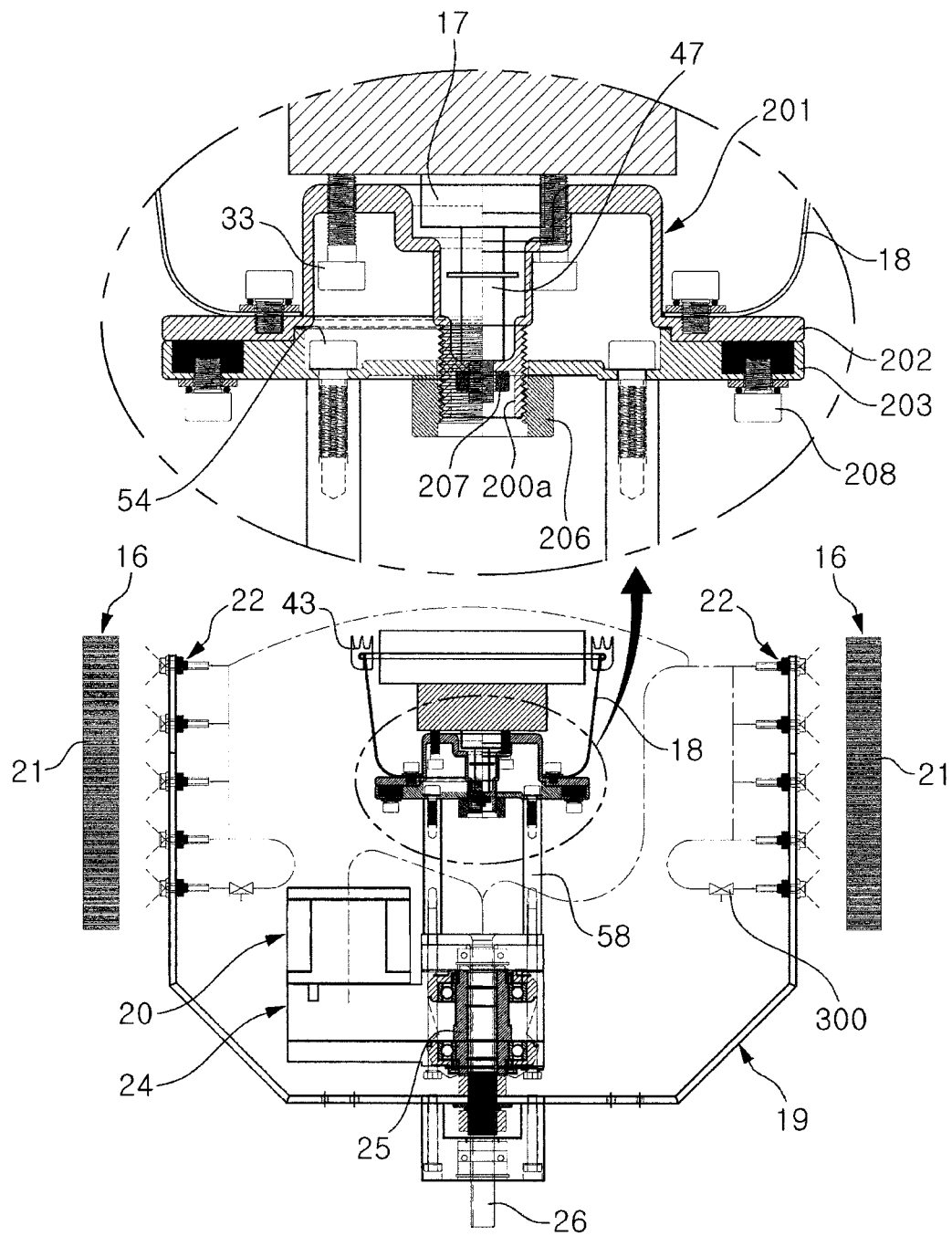
FIG. 13 is a cross-sectional view showing the assembled state of the washing and sterilizing module show in FIG. 12.
Figure 24:
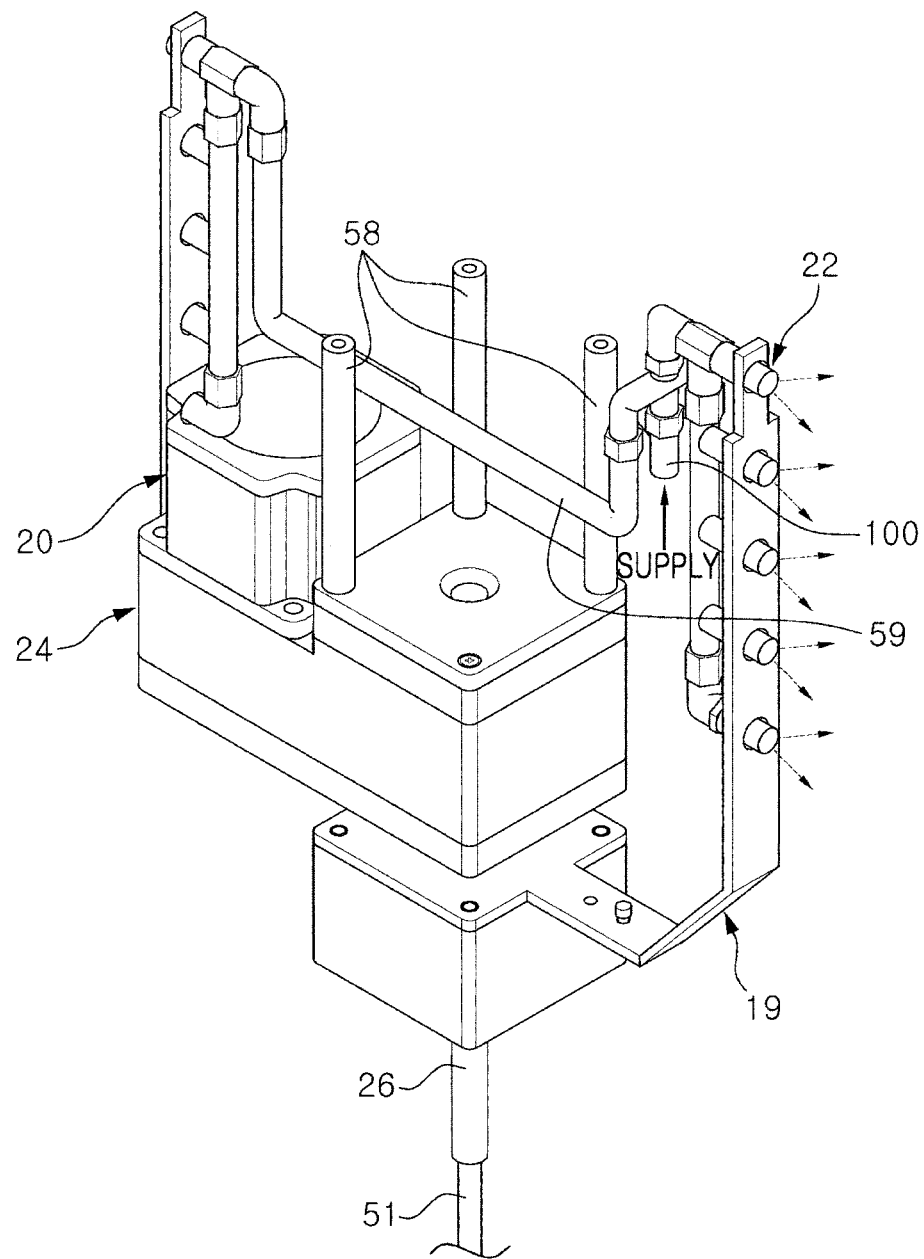
FIG. 24 is a view showing an exemplary modification of a spraying nozzle according to an embodiment of the present disclosure.

Referring to FIGS. 12, 13, and 24, a module for automatically washing and sterilizing a heat exchanger of a system air conditioner that is easily attached and detached, according to an embodiment (a first embodiment) of the present disclosure is designed to automatically wash out contaminants such as dust, grease, mold, and bacteria collected in the heat exchanger with a blowing fan separated from a fan motor in a system air conditioner, and to sterilize the heat exchanger.

The module includes: a metal housing 201 that is detachably fixed to a shaft 47 of a fan motor 17 by a fastening nut 207 and has a fastening portion 200 (male thread portion) on a bottom thereof;

a motor protection cover 18 that is fixed to the top of a flange 202 of the housing 201 to prevent detergent liquid or washing water, which is sprayed to wash a cooling fin 21, from flying to the fan motor 17;

a spray nozzle support 19 that has a spray nozzle 22 mounted thereon to spray detergent liquid, steam, washing water, and hot air, which are selectively supplied through a first supply hose 51 (e.g., a high-temperature high-pressure hose or a silicon hose) from the ground, to the cooling fin 21 (which is the cooling fin of the system air conditioner 16), inside which a driving motor 20 rotating forward and backward and a fixing plate 203 mounted on a fixing rod 58 (e.g., three fixing rods are used) having a lower portion coupled to a reducer 24 connected to the driving motor 20 are disposed, and that is connected to a rotary shaft 25 of the reducer 24 to be rotated forward and backward by the driving motor 20;

a magnet 204 (e.g., four magnets are used in a cross shape) that is fixed to the fixing plate 203 by a fixing bolt 208 to temporarily fix the fixing plate 203 by bringing the fixing plate 203 in close contact with the bottom of a flange 202; and a fastening nut 206 that is thread-fastened to a fastening portion 200 disposed through a coupling hole 205 of the fixing plate 203 and detachably fixes the spray nozzle support 19 to the housing 201.

The module includes an anti-rotation fixing bolt 33 having an end supported to the bottom of the fan motor 17 through a top plate of the housing to be able to prevent rotation of the housing 201 having the motor protection cover due to torque of the spray nozzle support 19 when the cooling fin 21 is washed out and sterilized.

The module includes a packing 43 disposed on the upper end of the motor protection cover 18 and coming in close contact with a ceiling panel on which the air conditioner is installed to prevent detergent liquid or washing water sprayed to wash the cooling fin 21 from flying to the fan motor 17.

The module includes a shut-off valve 300 opening and closing the channel of the lowermost spray nozzle of the spray nozzles 22, maintaining a locking mode when the height of the cooling fin 21 of the heat exchange is small, and maintaining an opening mode when the height of the cooling fin 21 of the cooling mode is relatively large.

That is, when the height of the cooling fin 21 is large (the size of the heat exchanger is small), the top spray nozzles (four spray nozzles in the figures) of the spray nozzles 22 is always maintained in the opening mode and the bottom spray nozzle is maintained in the locking mode. However, when the height of the cooling fin 21 is large (the size of the heat exchanger is relatively large), all of five spray nozzles 22 are maintained in the opening mode.

Since opening and closing the channels of the spray nozzles using the shut-off valve 300 is generally used in the field of the present disclosure, the configuration for this operation is not described in detail.

The module includes a hollow shaft 26 that is disposed through the rotary shaft 25 of the reducer 24 but is not rotated to pass the first supply hose 51 and a power cable for supplying power to the driving motor 20 to be able to prevent twisting of the first supply hose 51 and the power cable (not shown) when the spray nozzle support 19 are repeatedly rotated forward and backward in a predetermined angle range.

Hereafter, an example of using the module for automatically washing and sterilizing a heat exchanger of a system air conditioner that is easily attached and detached, according to an embodiment (first embodiment) of the present disclosure is described with reference to the accompanying drawings.

As shown in FIGS. 12, 13, and 24, the fan motor 17 is separated from the blowing fan (not shown) to wash out contaminants such as dust, grease, mold, and bacteria collected on the cooling fin 21 of the heat exchanger of the system air conditioner 16.

A coupling hole in the fastening portion 200 protruding from the bottom of the housing 201 is fitted on the shaft 47 of the fan motor 17. The motor protection cover 18 is mounted on the top of a flange 202 of the housing 201 to prevent detergent liquid or washing water, which is sprayed to wash a cooling fin 12, from flying to the fan motor 17.

The motor protection cover 18 is mounted first on the flange 202 and then the housing 201 may be fixed by the fastening nut 207 fitted on the shaft 47 of the fan motor 17.

The fastening nut 207 fixing the housing 201 by being thread-fastened to the shaft 47 is received in a groove 200a formed at a lower portion inside the fastening portion 200 not to be exposed to the outside.

The motor protection cover 18 is brought in close contact with the ceiling panel on which the air conditioner is installed, by the packing 43 mounted at the upper end thereof and can prevent detergent liquid, steam, washing water, and hot air from flying to the fan motor.

A worker can detachably fix alone the driving motor 20, the reducer 24, and the spray nozzle support 19 having a plurality of spray nozzles 22 to the housing 201.

In detail, the fixing plate 203 is mounted on the fixing rod 58 mounted on the reducer 24, by the fixing bolt 54. The magnet 204 received in the seat groove 203a formed on the top of the fixing plate 203 is fastened by the fixing bolt 208.

The fixing plate 203 mounted on the fixing rod 58 is lifted toward the housing 201 and then the top of the fixing plate 203 is brought in close contact with the bottom of the flange 202 of the metal housing 201, whereby the fixing plate 203 is attached to the bottom of the flange 202 made of metal by the magnetism of the magnet 204.

Accordingly, the fixing plate 203 can be temporarily fixed to the flange 202 of the housing 201. That is, the fixing plate 203 is prevented from dropping from the flange 202 by the magnetism of the magnet 204 of the fixing plate 203 attached to the flange 202 of the housing 201.

As described above, when the fixing plate 203 is temporarily fixed to the flange 202, the fastening portion 200 protruding from the bottom of the housing 201 passes through the coupling hole 205 formed at the center of the fixing plate 203.

Accordingly, the fastening nut 206 is thread-fastened to the fastening portion 200 from under the coupling hole 205 of the fixing plate 203, whereby the fixing plate 203 can be completely fixed to the housing 201.

The configuration of a rotary module for washing and sterilizing a heat exchange except for the housing 201 that has the motor protection cover 18 fixed to the flange 202 and detachably fixed to the shaft 47 of the fan motor 17 by the fastening nut 207, and the fixing plate 203 that is mounted on the fixing rod 58 by the fixing bolt 54, is supported by the flange 202 of the housing 201, and detachably fixes the spray nozzle support 19 to the housing 201 is applied substantially in the same way as the system for automatically washing and sterilizing the heat exchange of a system air conditioner disclosed in Korean Patent Application No. 10-2020-0122414 by the applicant(s). Accordingly, the configuration and operation thereof are not described.

Figure 14:
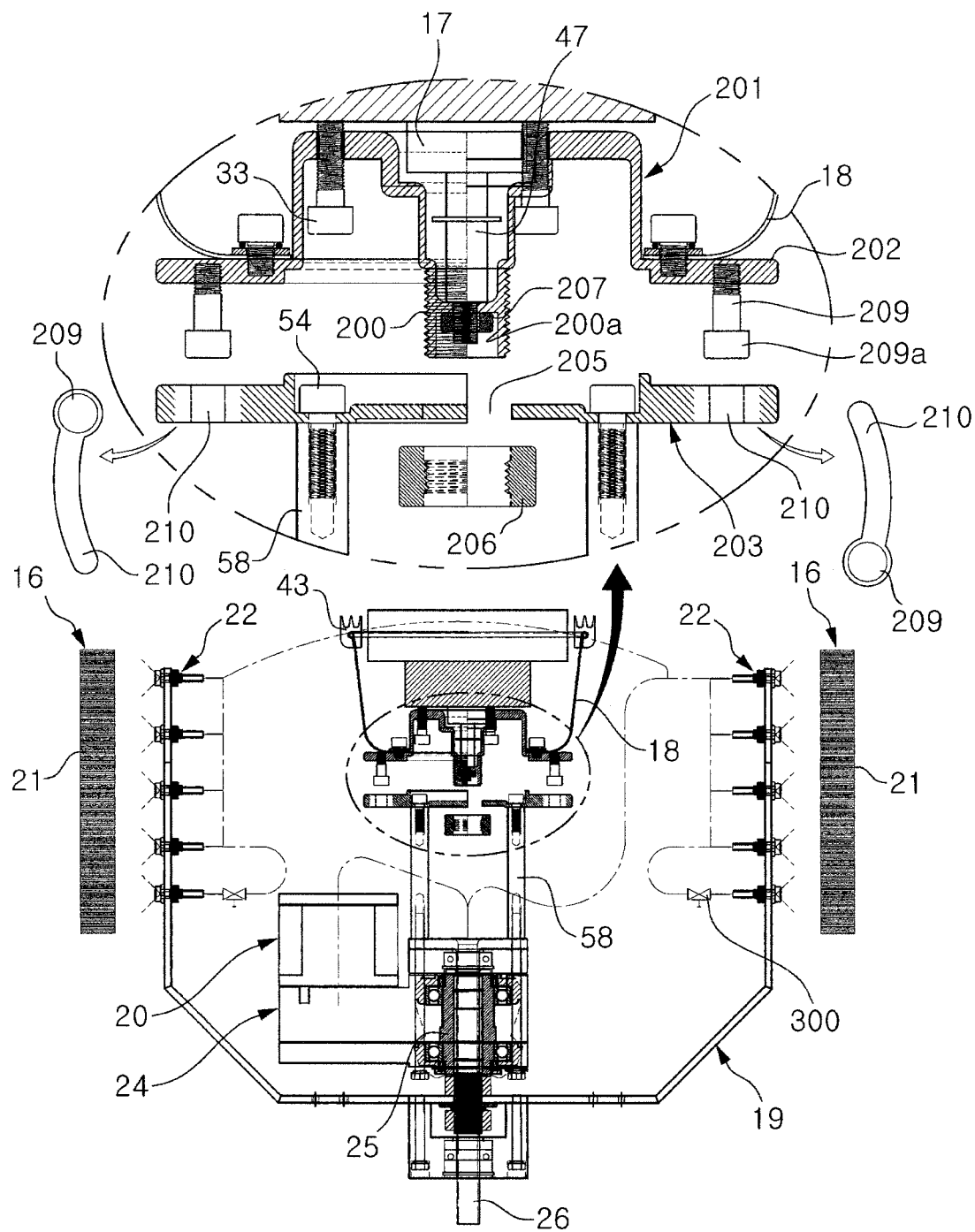
FIG. 14 is a cross-sectional view showing main parts of a module for washing and sterilizing a heat exchanger of a system air conditioner according to another exemplary embodiment of the present disclosure.
Figure 15:
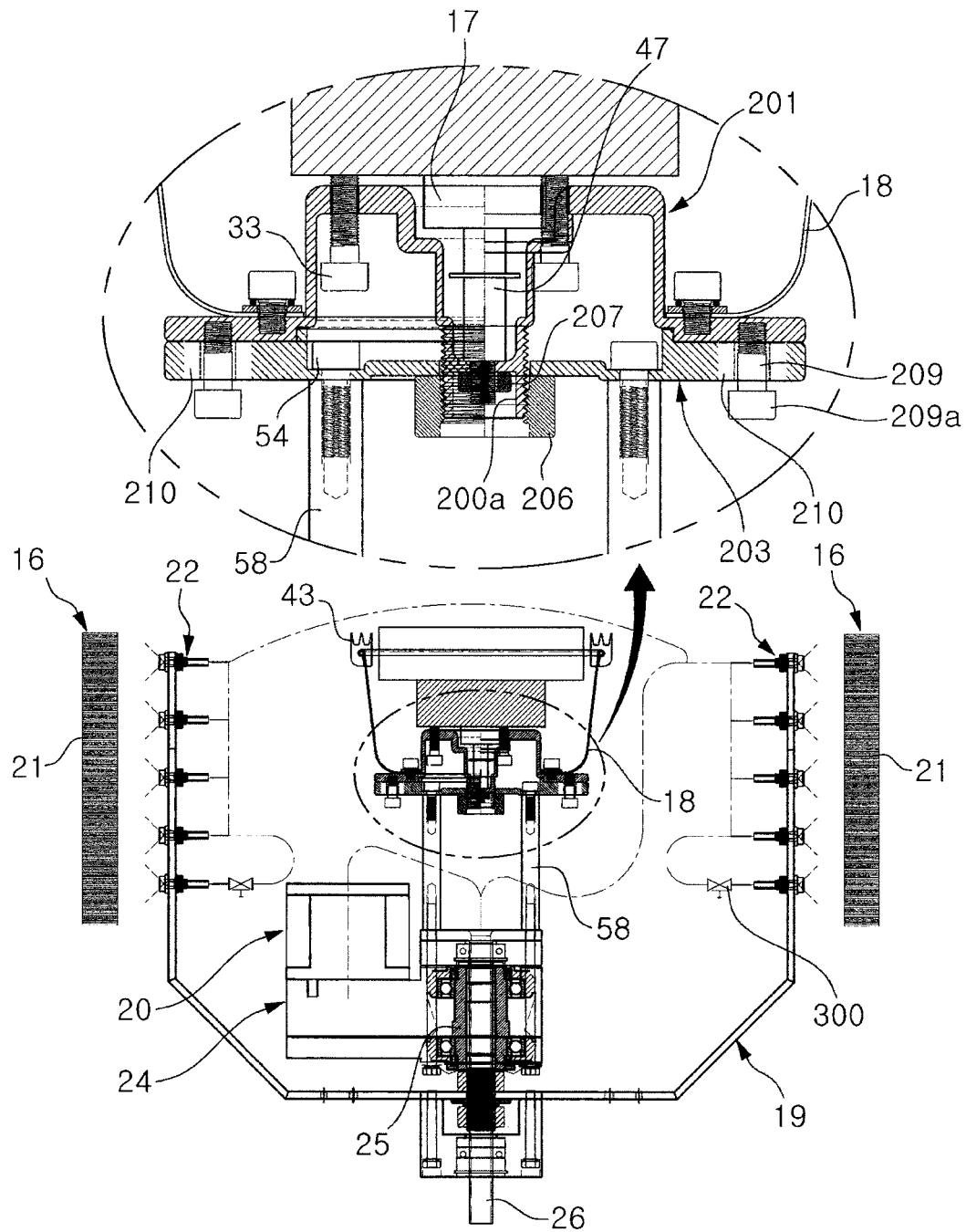
FIG. 15 is a cross-sectional view showing the assembled state of the washing and sterilizing module show in FIG. 14.

Referring to FIGS. 14, 15, and 24, a module for automatically washing and sterilizing a heat exchanger of a system air conditioner that is easily attached and detached, according to another embodiment (a second embodiment) of the present disclosure is designed to automatically wash out contaminants such as dust, grease, mold, and bacteria collected in the heat exchanger with a blowing fan separated from a fan motor in a system air conditioner, and to sterilize the heat exchanger.

The module includes: a housing 201 that is detachably fixed to a shaft 47 of a fan motor 17, that has a fastening portion 200 protruding from the bottom thereof, and to which fastening bolts 209 are fastened to face the bottom thereof with heads 209 spaced apart from the bottom;

a motor protection cover 18 that is fixed to the top of a flange 202 of the housing 201 to prevent washing water or detergent liquid, which is sprayed to wash a cooling fin 12, from flying to the fan motor 17;

a spray nozzle support 19 that has a spray nozzle 22 mounted at an upper portion thereof to spray detergent liquid, steam, washing air, and hot air, which are selectively supplied through a first supply hose 51 from the ground, to the cooling fin 21, inside which a driving motor 20 rotating forward and backward and a fixing plate 203 mounted on a fixing rod 58 coupled to a reducer 24 connected to the driving motor 20 are disposed, and that is rotated forward and backward by the driving motor 20, in which oblong holes 210 are formed in an arc shape to face each other in the fixing plate 203 and the oblong holes 210 are fitted on the fastening bolts 209 so that the fixing plate 203 is temporarily fixed to the heads 209a without dropping from the housing 201 when the fixing plate 203 is swung at a predetermined angle; and a fastening nut 206 that is thread-fastened to a fastening portion 200 disposed through a coupling hole 205 of the fixing plate 203 and detachably fixes the spray nozzle support 19 to the housing 201.

Hereafter, an example of using the module for automatically washing and sterilizing a heat exchanger of a system air conditioner that is easily attached and detached, according to an embodiment (second embodiment) of the present disclosure is described with reference to the accompanying drawings.

As shown in FIGS. 14, 15, and 24, the coupling hole in the fastening portion 200 (make thread portion0 protruding from the bottom of the housing 201 is fitted on the shaft 47 of the fan motor 17 with the blowing fan separated, and then the housing 201 can be fixed to the shaft 47 by a fastening nut 207 received in a groove 200a formed under the fastening portion 200.

The motor protection cover 18 is mounted on the flange 202 of the housing 201 before the housing 201 is fixed to the shaft 47.

A worker can detachably fix alone the driving motor 20, the reducer 24, and the spray nozzle support 19 having a plurality of spray nozzles 22 to the housing 201.

In detail, the fixing plate 203 is fixed to the upper end of the fixing rod 58 mounted on the reducer 24 by a fixing bolt 54 and then coupling holes (the holes in which the heads 209a of the fastening bolts 209 are fitted) at a side of the arc-shaped oblong holes 210 formed to face each other in the fixing plate 203 (the width of the oblong hole is larger than the diameter of the fastening bolt 209 and smaller than the diameter of the head 209a) are fitted on the fastening bolts 209 formed on the bottom of the flange 202.

When the fixing plate 203 of which the oblong holes 210 are fitted on the fastening bolts 209 of the flange 202 is swung at a predetermined angle, the fixing plate 203 is prevented from dropping from the flange 202 because the bottom of the fixing plate 203 is seated on the heads 209a of the fastening bolts 209.

Accordingly, the fixing plate 203 can be temporarily fixed to the flange 202.

As described above, when the fixing plate 203 is temporarily fixed to the fastening bolts 209 of the flange 202, the fastening portion 200 protruding from the bottom of the housing 201 passes through the coupling hole 205 formed at the center of the fixing plate 203.

Accordingly, the fastening nut 206 is thread-fastened to the fastening portion 200 from under the coupling hole 205 of the fixing plate 203, whereby the fixing plate 203 can be completely fixed to the housing 201.

The configuration of the module for washing a sterilizing the heat exchange of an air conditioner except for the fastening bolts 209 fastened to each other to the bottom of the housing 201 fixed to the shaft 47 of the fan motor 17, and the oblong holes 210 formed in the fixing plate 203 fixed to the upper end of the spray nozzle support 19 and temporarily fixing the fixing plate 203 to the flange 202 by being seated on the heads 209a of the fastening bolts 209 when the fixing plate 203 coupled to the fastening bolts 209 is swung at a predetermined angle, is applied substantially in the same as the configuration of an embodiment (first embodiment). Accordingly the configuration and the operation thereof are not described in detail.

Figure 16:
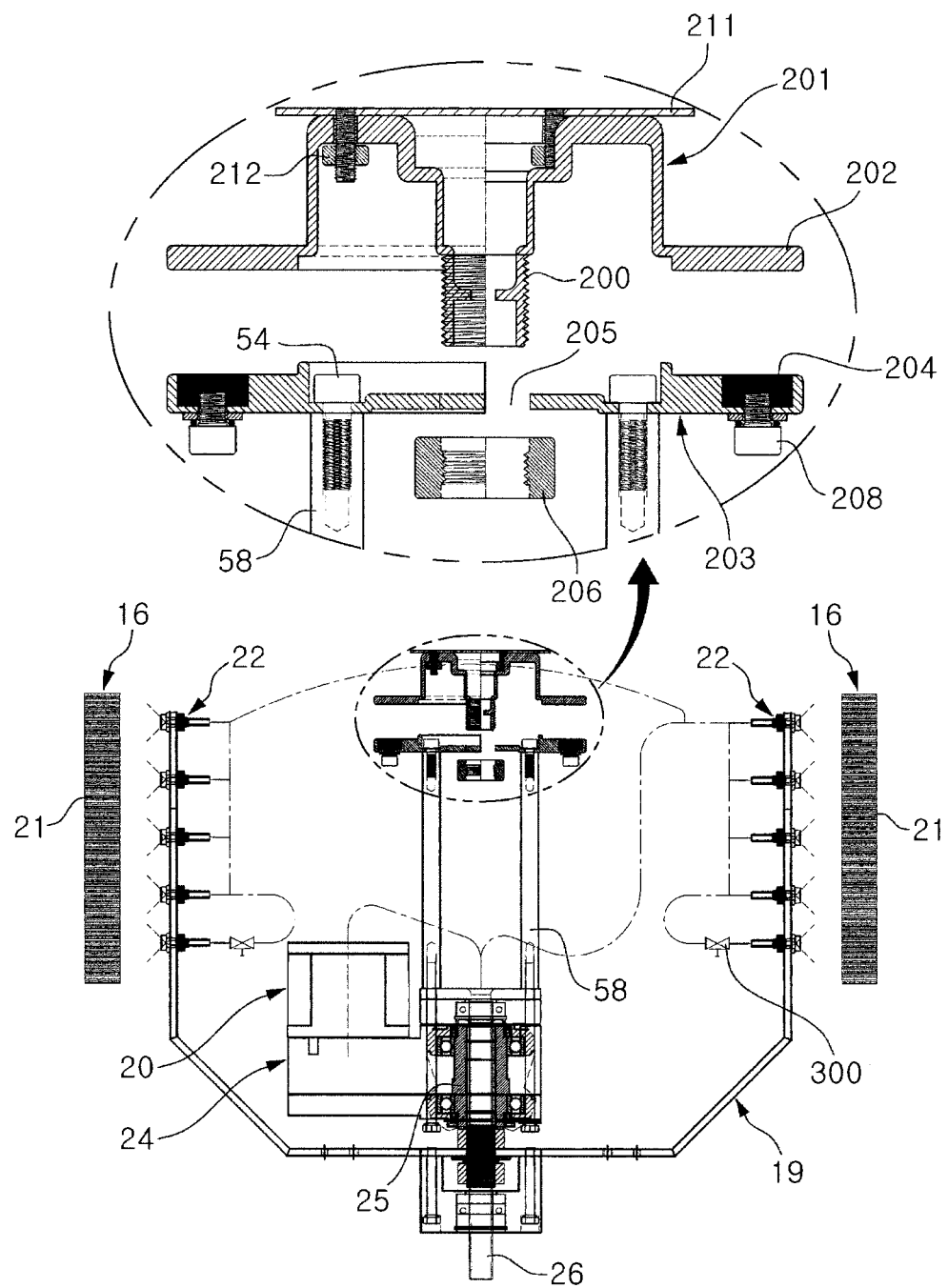
FIG. 16 is a cross-sectional view showing main parts of a module for washing and sterilizing a heat exchanger of a system air conditioner according to another exemplary embodiment of the present disclosure.
Figure 17:
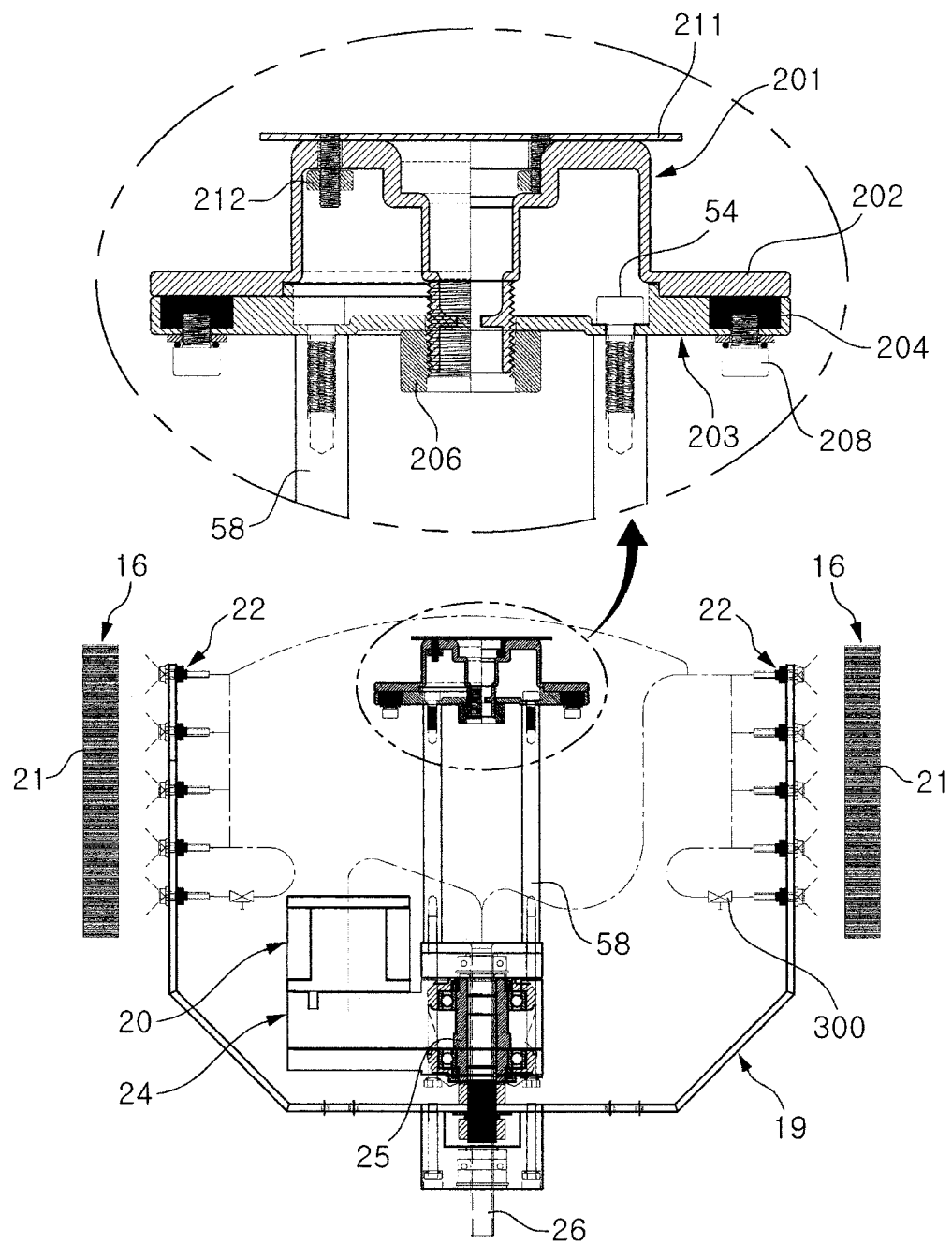
FIG. 17 is a cross-sectional view showing the assembled state of the washing and sterilizing module show in FIG. 16.

Referring to FIGS. 16, 17, and 24, a module for automatically washing and sterilizing a heat exchanger of a system air conditioner that is easily attached and detached, according to another embodiment (a third embodiment) of the present disclosure is designed to automatically wash out contaminants collected on the cooling fin of a heat exchanger with a fan motor separated in a system air conditioner, and to sterilize the cooling fin.

The module includes: a fixing board 211 mounted on a ceiling panel (not shown) on which the air conditioner 16 installed;

a metal housing 210 detachably fixed to the bottom of the fixing board 211 by a fastening nut 212 and having a fastening portion 200 protruding from the center of the bottom thereof;

a spray nozzle support 19 that has a spray nozzle 22 mounted at an upper portion thereof to spray detergent liquid, steam, washing air, and hot air, which are selectively supplied through a first supply hose 51 from the ground, to the cooling fin 21, inside which a driving motor 20 rotating forward and backward and a fixing plate 203 mounted on a fixing rod coupled to a reducer 24 connected to the driving motor 20 are disposed, and that is rotated forward and backward by the driving motor 20;

a magnet 204 disposed on the fixing plate 203 to temporarily fix the fixing plate 203 by bringing the top of the fixing plate 203 in close contact with the bottom of a flange 202 of the housing 201; and a fastening nut 206 that is thread-fastened to a fastening portion 200 disposed through a coupling hole 205 of the fixing plate 203 and detachably fixes the spray nozzle support 19 to the housing 201.

Hereafter, an example of using the module for automatically washing and sterilizing a heat exchanger of a system air conditioner that is easily attached and detached, according to another embodiment (third embodiment) of the present disclosure is described with reference to the accompanying drawings.

As shown in FIGS. 16, 17, and 24, the top of the housing 201 is brought in close contact with the bottom of the fixing board 211 mounted on a ceiling panel with the fan motor 17 of the system air conditioner 16 separated, and the housing 201 is fixed by a fastening nut 212.

The fixing plate 203 is mounted at the upper end of the fixing rod 58 mounted on the reducer 24, by the fixing bolt 54. The magnet 204 received in the seat groove 203*a* formed on the top of the fixing plate 203 is fastened by the fixing bolt 208.

The fixing plate 203 mounted on the fixing rod 58 is lifted toward the housing 201 and then the top of the fixing plate 203 is brought in close contact with the bottom of the flange 202 of the metal housing 201, whereby the fixing plate 203 is attached to the flange 202 made of metal by the magnetism of the magnet 204.

That is, the fixing plate 203 can be temporarily fixed to the flange 202.

As described above, when the fixing plate 203 is temporarily fixed in close contact with the bottom of the flange 202 of the housing 201, the fastening portion 200 protruding from the bottom of the housing 201 passes through the coupling hole 205 formed at the center of the fixing plate 203.

Accordingly, the fastening nut 206 is thread-fastened to the fastening portion 200 (male thread portion) from under the coupling hole 205 of the fixing plate 203, whereby the fixing plate 203 can be completely fixed to the housing 201.

The configuration of the rotary module for washing and sterilizing the heat exchange of an air conditioner except for the fixing board 211 mounted at a position where the fan motor is separated from the ceiling panel on which the air conditioner 16 is installed, and the fixing plate 203 mounted at the upper end of the fixing rod having the spray nozzle 22 and temporarily fixed with the top in close contact with the bottom of the flange 202 of the housing 201 by the magnetism of the magnet 204, is applied substantially in the same way as the configuration of an embodiment (first embodiment). Accordingly, the configuration and the operation thereof are not described in detail.

Figure 18:
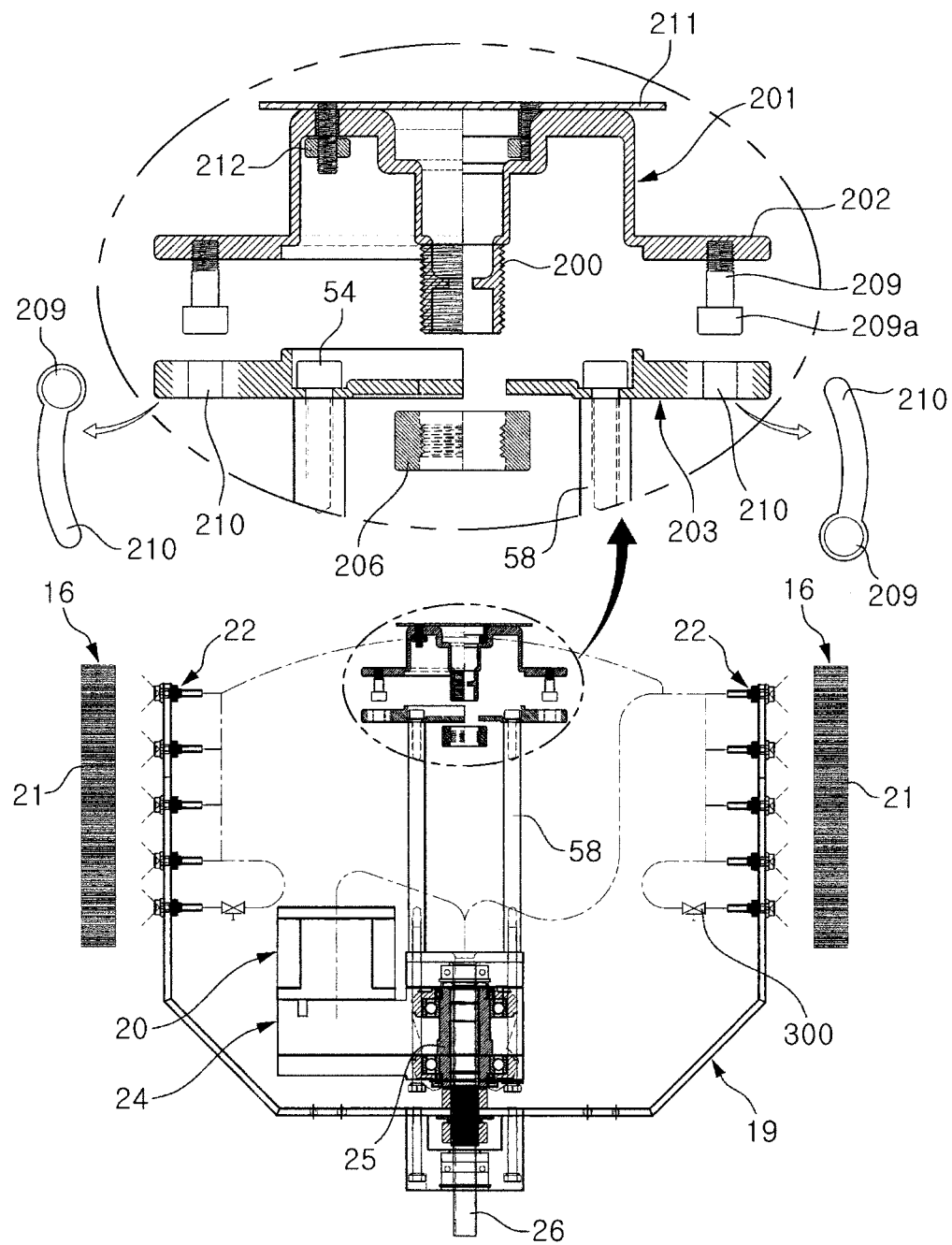
FIG. 18 is a cross-sectional view showing main parts of a module for washing and sterilizing a heat exchanger of a system air conditioner according to another exemplary embodiment of the present disclosure.
Figure 19:
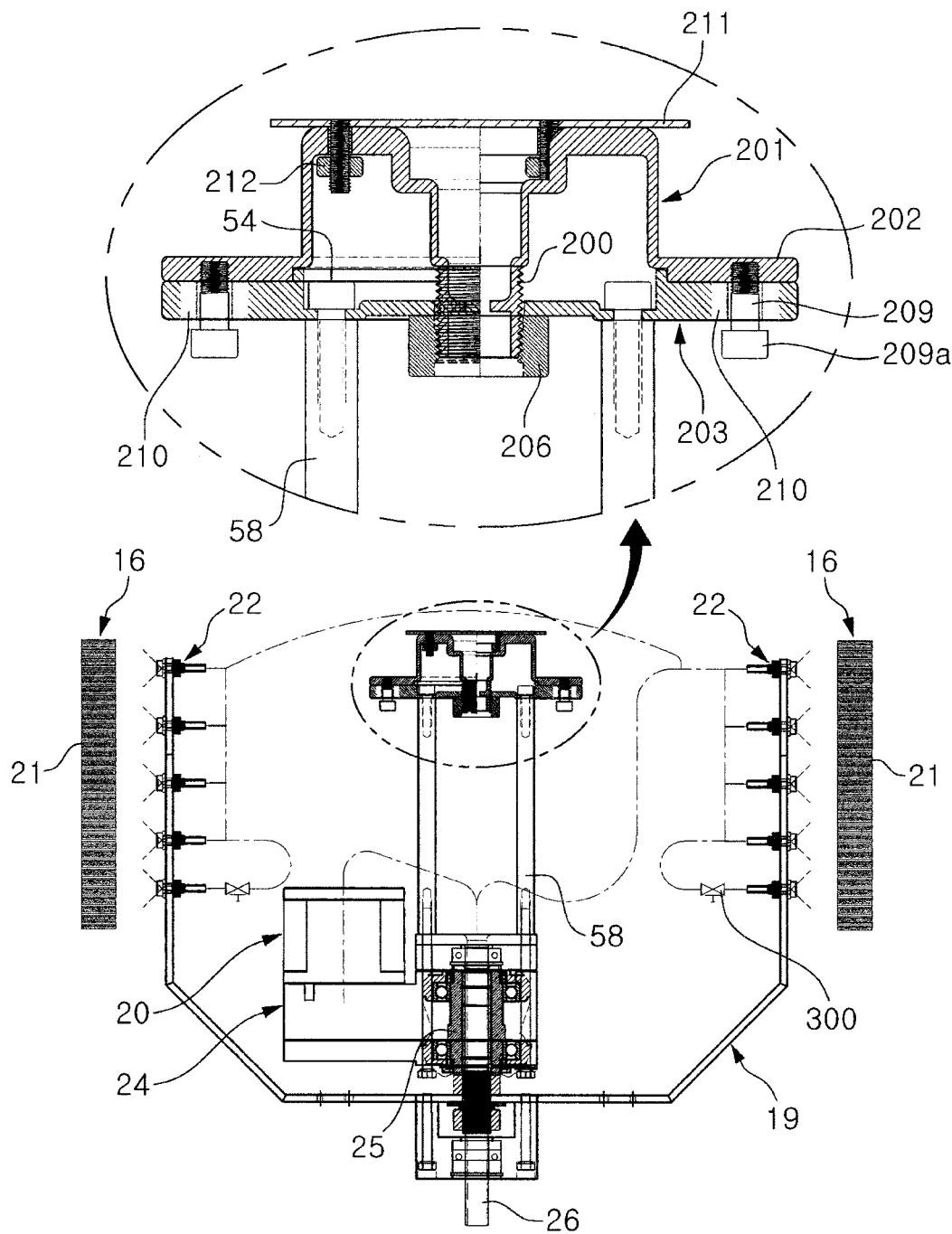
FIG. 19 is a cross-sectional view showing the assembled state of the washing and sterilizing module show in FIG. 18.

Referring to FIGS. 18, 19, and 24, a module for automatically washing and sterilizing a heat exchanger of a system air conditioner that is easily attached and detached, according to another embodiment (a fourth embodiment) of the present disclosure is designed to automatically wash out contaminants collected on the cooling fin of a heat exchanger with a fan motor separated in a system air conditioner, and to sterilize the cooling fin.

The module includes: a fixing board 211 mounted on the ceiling panel on which the heat exchanger is installed;

- a housing 201 that is detachably fixed to the bottom of the fixing board 211, that has a fastening portion 200 protruding from the center of the bottom thereof, and to which fastening bolts 209 are fastened to face the bottom thereof with heads 209 spaced apart from the bottom;
- a spray nozzle support 19 that has a spray nozzle 22 mounted at an upper portion thereof to spray detergent liquid, steam, washing air, and hot air, which are selectively supplied through a first supply hose 51 from the ground, to the cooling fin 21, inside which a driving motor 20 rotating forward and backward and a fixing plate 203 mounted on a fixing rod 58 coupled to a reducer 24 are disposed, and that is rotated forward and backward by the driving motor 20,
- in which oblong holes 210 are formed in an arc shape to face each other in the fixing plate 203 and the oblong holes 210 are fitted on the fastening bolts 209 so that the fixing plate 203 is temporarily fixed to the heads 209*a* without dropping from the housing 201 when the fixing plate 203 is swung at a predetermined angle; and
- a fastening nut 206 that is thread-fastened to a fastening portion 200 disposed through a coupling hole of the fixing plate 203 and detachably fixes the spray nozzle support 19 to the housing 201.

Hereafter, an example of using the module for automatically washing and sterilizing a heat exchanger of a system air conditioner that is easily attached and detached, according to another embodiment (fourth embodiment) of the present disclosure is described with reference to the accompanying drawings.

As shown in FIGS. 18, 19, and 24, the top of the housing 201 is brought in close contact with the bottom of a fixing plate 211 mounted on a ceiling panel with the fan motor 17 of the system air conditioner 16 separated, and the housing 201 is fixed by a fastening nut 212.

The fixing plate 203 is fixed to the upper end of the fixing rod 58 mounted on the reducer 24 by the fixing bolt 54 and then the coupling holes of the oblong holes 210 formed in an arc shape to face each other in the fixing plate 203 are fitted to the fastening bolts 209 formed on the bottom of the flange 202.

When the fixing plate 203 of which the oblong holes 210 are fitted on the fastening bolts 209 of the flange 202 is swung at a predetermined angle, the fixing plate 203 is prevented from dropping from the flange 202 because the bottom of the fixing plate 203 is seated on the heads 209*a* of the fastening bolts 209.

That is, the fixing plate 203 can be temporarily fixed to the flange 202.

As described above, when the fixing plate 203 is temporarily fixed to the fastening bolts 209 of the flange 202, the fastening portion 200 protruding from the bottom of the housing 201 passes through the coupling hole 205 formed at the center of the fixing plate 203.

Accordingly, the fastening nut 206 is thread-fastened to the fastening portion 200 (male thread portion) from under the coupling hole 205 of the fixing plate 203, whereby the fixing plate 203 can be completely fixed to the housing 201 mounted on the fixing board 211 by the fastening nut 212.

The rotary module for washing and sterilizing the heat exchanger of an air conditioner except for the fixing board 211 mounted on the ceiling panel with the fan motor 17 separated and having the housing 201 mounted with the top of the housing in close contact with the fixing board, and the oblong holes 210 being able to temporarily fix the fixing plate 230 to the housing 201 when the fixing plate 203 coupled to the heads 209*a* of the fastening bolts 209 formed on the flange 202 of the housing 201 is swung at a predetermined angle, is applied substantially in the same way as the configuration of another embodiment (second embodiment). Accordingly, the configuration and the operation thereof are not described in detail.

Figure 20:
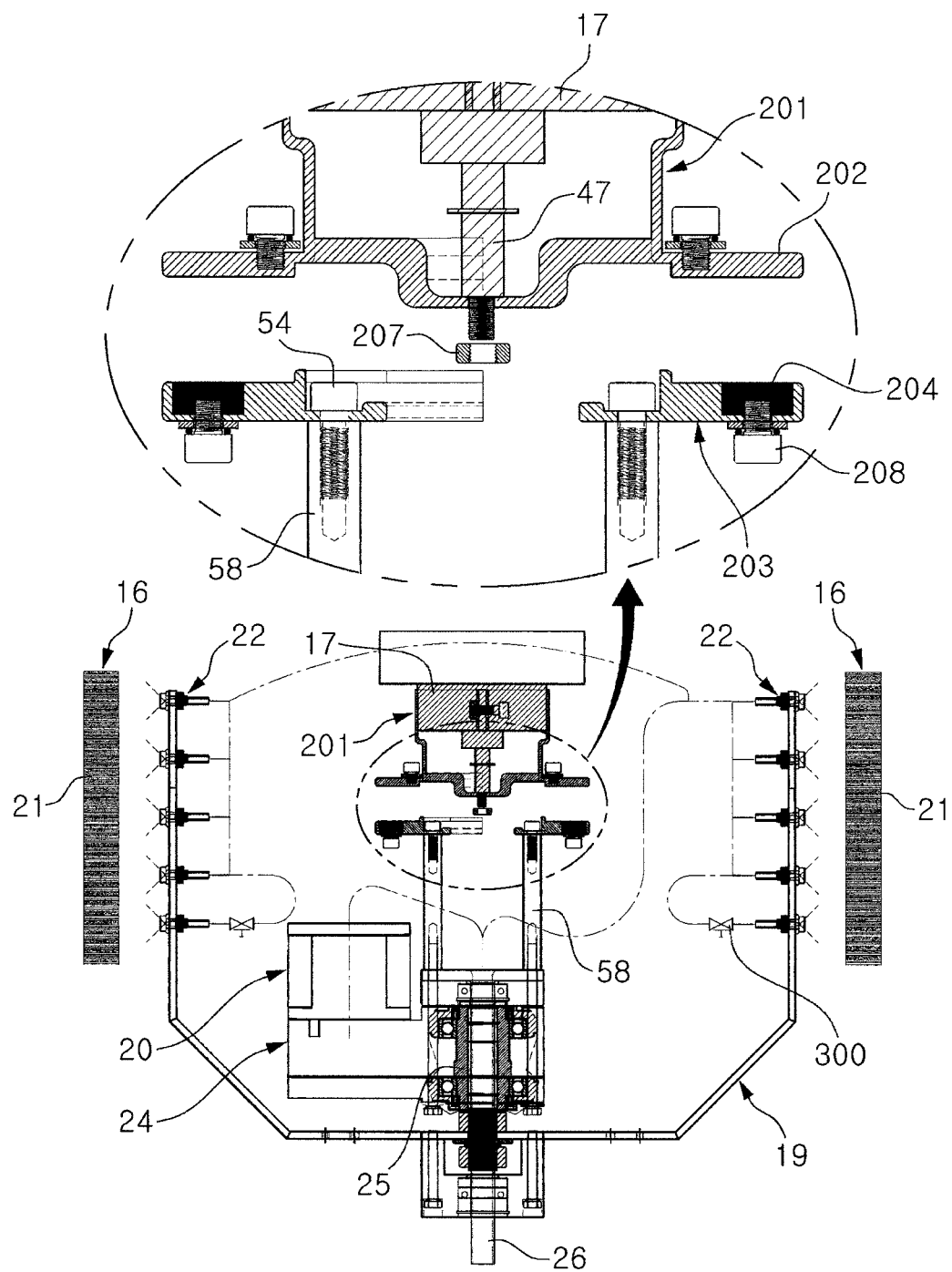
FIG. 20 is a cross-sectional view showing main parts of a module for washing and sterilizing a heat exchanger of a system air conditioner according to another exemplary embodiment of the present disclosure.
Figure 21:
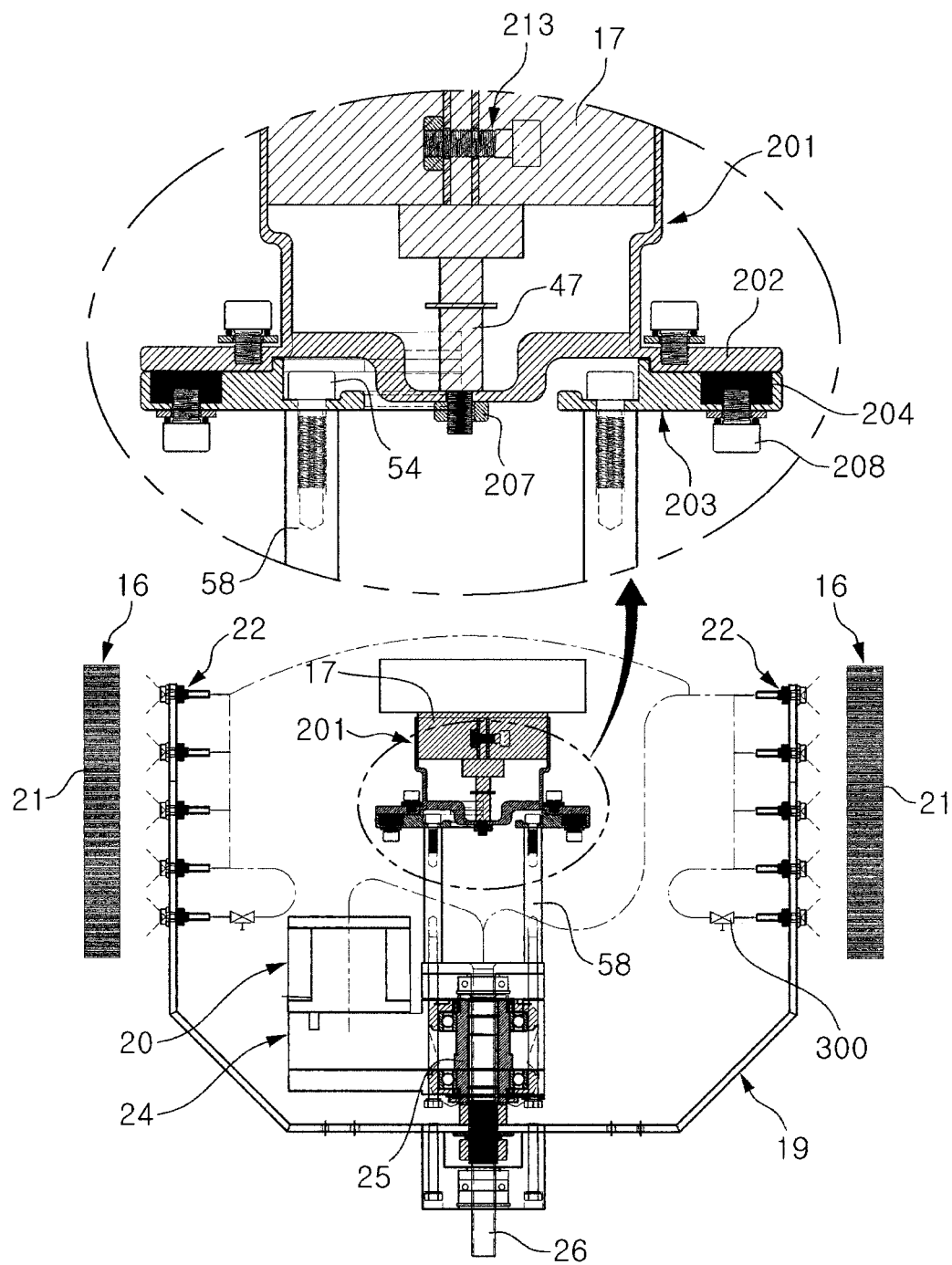
FIG. 21 is a cross-sectional view showing the assembled state of the washing and sterilizing module show in FIG. 20.

Referring to FIGS. 20, 21, and 24, a module for automatically washing and sterilizing a heat exchanger of a system air conditioner that is easily attached and detached, according to another embodiment (a fifth embodiment) of the present disclosure is designed to automatically wash out contaminants collected on the cooling fin of a heat exchanger with a blowing fan separated from a fan motor in a system air conditioner, and to sterilize the cooling fin.

The module includes: a metal housing 201 that has a band disposed at an upper portion thereof to surround the outer surface of the fan motor 17 and fixed by a fastening member 213, has a lower portion detachably fixed by a fastening nut 207 thread-fastened to the shaft 47 of the fan motor 17 disposed through the coupling hole of the bottom plate, and prevents washing water or detergent liquid sprayed when the cooling fin 21 is washed from flying to the fan motor 17;
- a spray nozzle support 19 that has a spray nozzle 22 mounted at an upper portion thereof to spray detergent liquid, steam, washing air, and hot air, which are selectively supplied through a first supply hose 51 from the ground, to the cooling fin 21, inside which a driving motor 20 rotating forward and backward and a fixing plate 203 mounted on a fixing rod 58 coupled to a reducer 24 connected to the driving motor 20 are disposed, and that is rotated forward and backward by the driving motor 20; and
- a magnet 22 disposed on the fixing plate 203 to fix the fixing plate 203 by bringing the top of the fixing plate 203 in close contact with the bottom of a flange 202 of the housing 201.

Hereafter, an example of using the module for automatically washing and sterilizing a heat exchanger of a system air conditioner that is easily attached and detached, according to another embodiment (fifth embodiment) of the present disclosure is described with reference to the accompanying drawings.

As shown in FIGS. 20, 21, and 24, the fan motor 17 separated from the blowing fan (not shown) is surrounded by the upper band of the housing 201 and is detachably fixed by a fastening member 213 (a bolt or a nut). Accordingly, the housing 201 is prevented from dropping from the fan motor 17.

The fixing plate 203 is mounted at the upper end of the fixing rod 58 mounted on the reducer 24, by the fixing bolt 54. The magnet 204 received in the seat groove 203a formed on the top of the fixing plate 203 is fastened by the fixing bolt 208.

The fastening nut 207 is thread-fastened to the shaft 47 of the fan motor 17 disposed through the coupling hole formed through the center of the bottom of the housing 201, whereby the housing 201 can be detachably fixed to the shaft 47 of the fan motor 17.

The fixing plate 203 mounted on the fixing rod 58 is lifted toward the flange 202 of the housing 201 such that the top of the fixing plate 203 is brought in close contact with the bottom of the flange 202 of the metal housing 201, whereby the fixing plate 203 is detachably attached to the metal flange 202 by the magnetism of the magnet 204 fixed to the fixing plate 203.

The configuration of the rotary module for washing and sterilizing the heat exchange of an air conditioner except for the housing 201 surrounding and supporting the fan motor 17 with the band and detachably fixed by the fastening member 213, and the fixing plate 203 mounted at the upper end of the fixing rod 58 and temporarily fixed with the top in close contact with the bottom of the flange 202 of the housing 201 by the magnetism of the magnet 204, is applied substantially in the same way as the configuration of an embodiment (first embodiment). Accordingly, the configuration and the operation thereof are not described in detail.

Figure 22:
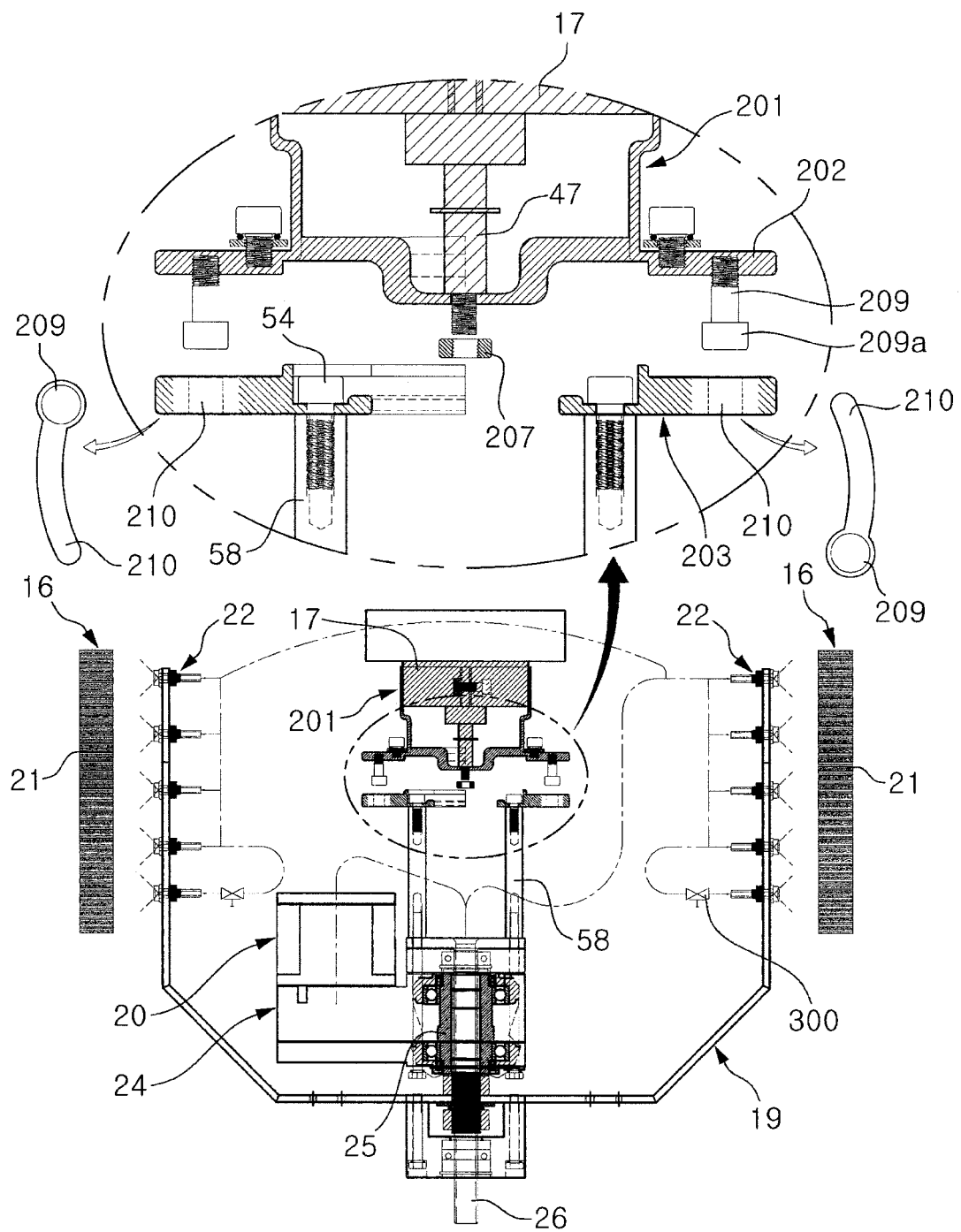
FIG. 22 is a cross-sectional view showing main parts of a module for washing and sterilizing a heat exchanger of a system air conditioner according to another exemplary embodiment of the present disclosure.
Figure 23:
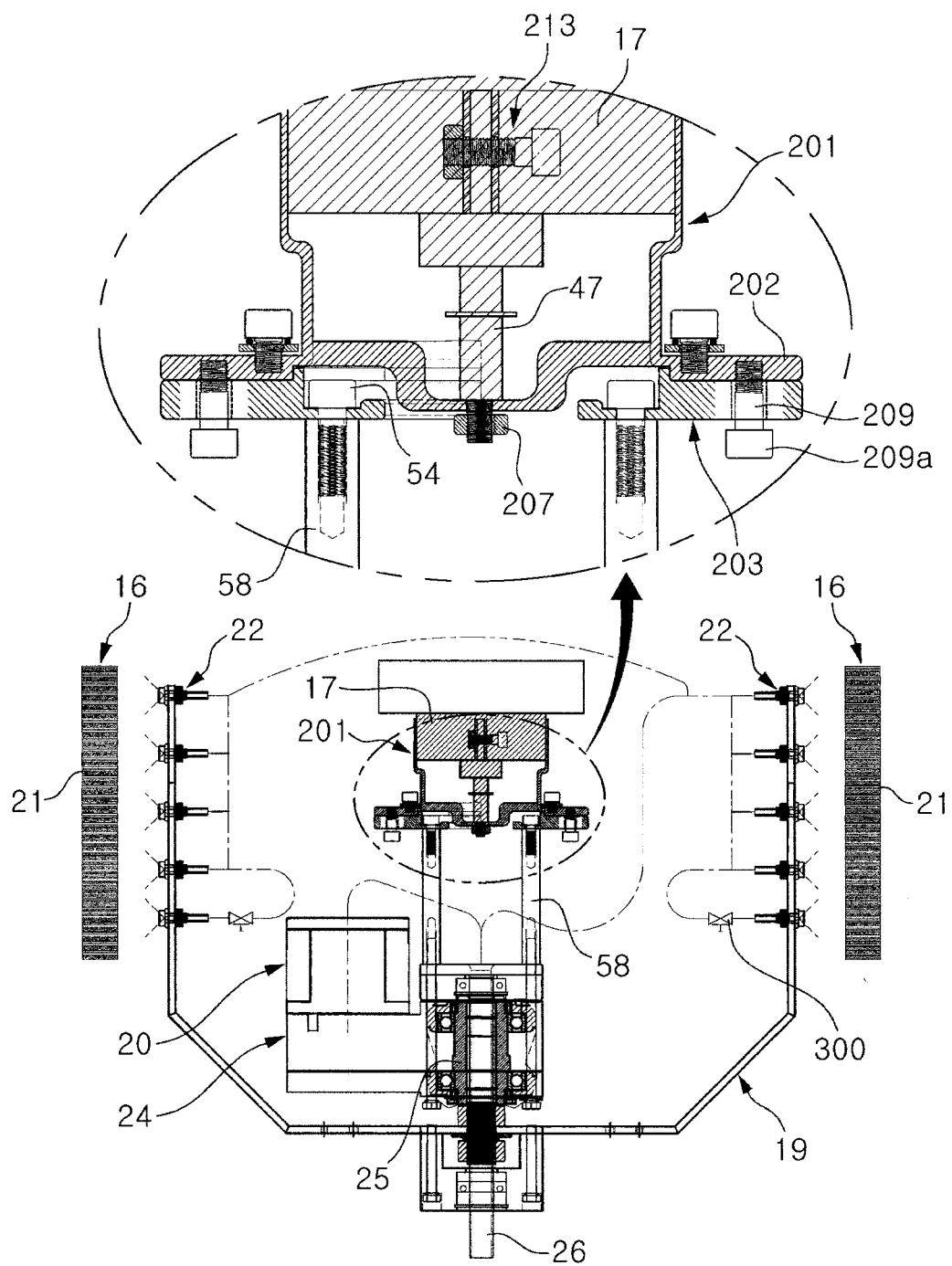
FIG. 23 is a cross-sectional view showing the assembled state of the washing and sterilizing module show in FIG. 22.

Referring to FIGS. 22, 23, and 24, a module for automatically washing and sterilizing a heat exchanger of a system air conditioner that is easily attached and detached, according to another embodiment (a sixth embodiment) of the present disclosure is designed to automatically wash out contaminants collected on the cooling fin of a heat exchanger with a blowing fan separated from a fan motor in a system air conditioner, and to sterilize the cooling fin.

The module includes: a housing 201 (e.g., which may be made of engineering plastic, plastic, etc.) that has a band disposed at an upper portion thereof to surround the outer surface of the fan motor 17 and fixed by a fastening member 213, has a lower portion detachably fixed by a fastening nut 207 thread-fastened to the shaft 47 of the fan motor 17 disposed through the coupling hole of the bottom plate, to which fastening bolts 209 are fastened to face the bottom thereof with heads 209 spaced apart from the bottom, and prevents washing water or detergent liquid sprayed when the cooling fin 21 is washed from flying to the fan motor 17; and
- a spray nozzle support 19 that has a spray nozzle mounted at an upper portion thereof to spray detergent liquid, steam, washing air, and hot air, which are selectively supplied through a first supply hose 51 from the ground, to the cooling fin 21, inside which a driving motor 20 rotating forward and backward and a fixing plate 203 mounted on a fixing rod 58 coupled to a reducer 24 connected to the driving motor 20 are disposed, and that is rotated forward and backward by the driving motor 20,
- in which oblong holes 210 are formed in an arc shape to face each other in the fixing plate 203 and the oblong holes 210 are fitted on the fastening bolts 209 so that the fixing plate 203 is seated on the heads 209a without dropping from the housing 201 when the fixing plate 203 is swung at a predetermined angle; and Hereafter, an example of using the module for automatically washing and sterilizing a heat exchanger of a system air conditioner that is easily attached and detached, according to another embodiment (sixth embodiment) of the present disclosure is described with reference to the accompanying drawings.

As shown in FIGS. 22, 23, and 24, the upper band of the housing 201 surrounds and supports the fan motor 17 and is detachably fixed by the fastening member 213.

The fastening nut 207 is thread-fastened to the shaft 47 of the fan motor 17 disposed through the coupling hole formed through the center of the bottom of the housing 201, whereby the housing 201 can be detachably fixed to the shaft 47 of the fan motor 17.

Accordingly, the housing 201 is prevented from dropping from the fan motor 17 due to shock, etc.

The fixing plate 203 is mounted on the upper end of the fixing rod 58 mounted on the reducer 24 by the fixing bolt 54 and then the coupling holes of the oblong holes 210 formed in an arc shape to face each other in the fixing plate 203 are fitted to the fastening bolts 209 formed on the bottom of the flange 202.

When the fixing plate 203 of which the oblong holes 210 are fitted on a side to the fastening bolts 209 is swung at a predetermined angle, the fixing plate 203 is prevented from dropping from the flange 202 because the bottom of the fixing plate 203 is seated on the heads 209a of the fastening bolts 209.

Accordingly, the housing 201 can be detachably fixed by the fastening member 213 fastening the band of the housing 201 that surround and supports the outer surface of the fan motor 17 and by the fastening nut 207 thread-fastened to the shaft 47 of the fan motor 17.

The rotary module for washing and sterilizing the heat exchanger of an air conditioner except for the housing 201 surrounding and fixing the fan motor 17 with the band and detachably fixed by the fastening member 213, and the oblong holes 210 formed at the upper end of the fixing rod 58, coupled to the heads 209*a* of the fastening bolts 209 formed on the flange 202 of the housing 201, and being able to fix the fixing plate 230 to the housing 201 when being swung at a predetermined angle, is applied substantially in the same way as the configuration of another embodiment (second embodiment). Accordingly, the configuration and the operation thereof are not described in detail.

The present invention was described with reference to embodiments herein, it should be understood that the present disclosure may be changed and modified in various ways by those skilled in the art without departing from the spirit and scope of the present disclosure described in the specification and the claims.

What is claimed is:

1. A system for automatically washing and sterilizing a heat exchanger of a system air conditioner, the system being designed to wash out contaminants including one of dust, grease, mold, and bacteria collected on a cooling fin of a heat exchanger with a blowing fan separated from a fan motor, and to sterilize the cooling fin with an indoor unit of the system air conditioner installed or embedded in a ceiling panel, in a system air conditioner including the fan motor, the blowing fan, and the heat exchanger, the system comprising:
    a washer body comprising an air compressor that is mounted therein, a compressed air tank that is connected to the air compressor, a detergent liquid tank, a detergent liquid-assistant heater, a washing water tank, a washing water-assistant heater, a pressure pump, a hot air generator, and a steam-heat generator;
    a washing module comprising a motor protection cover that surrounds the fan motor, a driving motor that can rotate forward and backward within a predetermined angle range, a reducer that has an upper end fixed to a lower end of a fixing rod fixed to the motor protection cover, and is connected to the driving motor, and a spray nozzle that is mounted on a spray nozzle support connected to a rotary shaft of the reducer to be rotatable within a predetermined angle range, and selectively receives and sprays compressed air, detergent liquid, hot washing water, room-temperature washing water, steam, and hot air, which are supplied from the compressed air tank, the detergent liquid tank, the washing water tank, a hot water generator, the steam generator, and the hot air generator, to the cooling fin;
    a waste water collection vinyl cover that has an upper opening fixed to the ceiling panel on which the system air conditioner is installed, is fixed at a portion of a bottom thereof to a lower end of a non-rotating hollow shaft, which is disposed through the rotary shaft of the reducer, not to sag, and collects contaminated waste water dropping when the cooling fin is washed by the spray nozzle; and
    a controller that controls the spray nozzle to selectively spray the compressed air, the detergent liquid, the hot washing water, the room-temperature washing water, and the steam, and the hot air to the cooling fin.

2. A system for automatically washing and sterilizing a heat exchanger of a system air conditioner, the system being designed to wash out contaminants including one of dust, grease, mold, and bacteria collected on a cooling fin of a heat exchanger with a fan motor separated, and to sterilize the cooling fin with an indoor unit of the system air conditioner installed or embedded in a ceiling panel, in a system air conditioner including the fan motor, a blowing fan, and the heat exchanger the system comprising:
    a washer body comprising an air compressor that is mounted therein, a compressed air tank that is connected to the air compressor, a detergent liquid tank, a detergent liquid-assistant heater, a washing water tank, a washing water-assistant heater, a pressure pump, a hot air generator, a steam-heat generator;
    a washing module comprising one or more fixing rods having an upper end fixed to a fixing plate on which the fan motor is mounted, a driving motor that can rotate forward and backward within a predetermined angle range, and a spray nozzle that is mounted on a spray nozzle support rotatably connected to a rotary shaft of a reducer fixed to a lower end of a fixing rod and connected to the driving motor, and selectively receives and sprays compressed air, detergent liquid, hot washing water, room-temperature washing water, steam, and hot air, which are supplied from the compressed air tank, the detergent liquid tank, the washing water tank, a hot water generator, the steam generator, and the hot air generator, to the cooling fin;
    a waste water collection vinyl cover that has an upper opening fixed to the ceiling panel on which the system air conditioner is installed, is fixed at a portion of a bottom thereof to a lower end of a non-rotating hollow shaft, which is disposed through the rotary shaft of the reducer, not to sag, and collects contaminated waste water dropping when the cooling fin is washed by the spray nozzle; and
    a controller that controls the spray nozzle to selectively spray the compressed air, the detergent liquid, the hot washing water, the room-temperature washing water, and the steam, and the hot air to the cooling fin.

3. The system of claim 1, wherein operation of the washing module is controlled to start and finish by operating any one of a notebook, a PC, a remote controller, and a control panel of the controller.

4. The system of claim 1, further comprising an anti-rotation fixing bolt formed on a bottom inside the motor protection cover and having an end supported on the bottom of a fixing plate of the fan motor through a thread-fastened fixing nut to be able to prevent the motor protection cover from being rotated by torque of the spray nozzle support when the washing module washes and sterilizes the cooling fin.

5. The system of claim 1, wherein the waste water collection vinyl cover is made of a transparent material so that it is possible to visually check a process of washing the cooling fin using the washing module or to take a picture using a camera mounted on a camera support of the controller.

6. The system of claim 1, wherein the motor protection cover further comprises a packing disposed on an edge of a top opening of the motor protection cover and fixed to a fan motor-fixing plate of the air conditioner to prevent washing water or cleansing liquid, which is sprayed to wash and sterilize the cooling fin by the washing module, from flying to the fan motor.

* * * * *